(12) United States Patent
Laborde et al.

(10) Patent No.: US 11,585,882 B2
(45) Date of Patent: Feb. 21, 2023

(54) SUPERPARAMAGNETIC PARTICLE IMAGING AND ITS APPLICATIONS IN QUANTITATIVE MULTIPLEX STATIONARY PHASE DIAGNOSTIC ASSAYS

(71) Applicant: Mars Sciences Limited, Grand Cayman (KY)

(72) Inventors: Ronald T. Laborde, San Diego, CA (US); Yu Ge, San Diego, CA (US); Kevin N. Walda, San Diego, CA (US)

(73) Assignee: Mars Sciences Limited, George Town (KY)

( * ) Notice: Subject to any disclaimer, the term of this patent is extended or adjusted under 35 U.S.C. 154(b) by 606 days.

(21) Appl. No.: 16/379,748

(22) Filed: Apr. 9, 2019

(65) Prior Publication Data

US 2019/0317167 A1  Oct. 17, 2019

Related U.S. Application Data

(60) Provisional application No. 62/664,946, filed on May 1, 2018, provisional application No. 62/655,828, filed on Apr. 11, 2018.

(51) Int. Cl.
*G01R 33/56* (2006.01)
*G01N 33/543* (2006.01)
(Continued)

(52) U.S. Cl.
CPC ...... *G01R 33/5601* (2013.01); *A61K 49/1878* (2013.01); *G01N 33/587* (2013.01); *G01R 33/07* (2013.01); *G01N 33/54326* (2013.01)

(58) Field of Classification Search
None
See application file for complete search history.

(56) References Cited

U.S. PATENT DOCUMENTS 4,933,092 A 6/1990 Aunet et al.
7,778,681 B2 8/2010 Gleich
(Continued)

FOREIGN PATENT DOCUMENTS

CN 101726535 A 6/2010
DE 102010009161 A1 8/2011
(Continued)

OTHER PUBLICATIONS

Baselt, D., "A biosensor based on magnetoresistance technology," Biosens Bioelectron., 13, 731-739 (1998).
(Continued)

*Primary Examiner* — Rebecca M Giere
*Assistant Examiner* — Xiaoyan Zou
(74) *Attorney, Agent, or Firm* — Mei & Mark LLP; Manni Li

(57) ABSTRACT

Superparamagnetic nanoparticle-based analytical method comprising providing a sample having analytes in a sample matrix, providing a point of care chip having analytical regions, each of which is a stationary phase having at least one or more sections, labeling each of the analytes with a superparamagnetic nanoparticle and immobilizing the labeled analytes in the stationary phase, providing an analytical device having a means for exciting the superparamagnetic nanoparticles in vitro and a means for sensing, receiving, and transmitting response of the excited superparamagnetic nanoparticles, placing the chip in the analytical device and exciting the superparamagnetic nanoparticles in vitro, sensing, receiving, and transmitting the response of the superparamagnetic nanoparticles, and analyzing the response and determining characteristic of the analytes, wherein the response of the superparamagnetic nanoparticles comprises harmonics. The present invention also pro-
(Continued)

vides the hybrid point of care chip and analyzer to be used in the analytical method.

10 Claims, 23 Drawing Sheets

(51) Int. Cl.
  *G01R 33/07* (2006.01)
  *A61K 49/18* (2006.01)
  *G01N 33/58* (2006.01)

(56) References Cited

U.S. PATENT DOCUMENTS

| | | | |
|---|---|---|---|
| 2004/0043479 | A1 | 3/2004 | Briscoe et al. |
| 2004/0130314 | A1* | 7/2004 | Bossoli ............... G01D 5/147 |
| | | | 324/207.2 |
| 2004/0248318 | A1 | 12/2004 | Weinberger et al. |
| 2005/0100930 | A1 | 5/2005 | Wang et al. |
| 2005/0106713 | A1 | 5/2005 | Phan et al. |
| 2005/0130292 | A1 | 6/2005 | Ahn et al. |
| 2006/0078986 | A1 | 4/2006 | Ly et al. |
| 2009/0278534 | A1 | 11/2009 | Kahlman |
| 2010/0200428 | A1 | 8/2010 | Choi et al. |
| 2010/0301850 | A1 | 12/2010 | Lenglet |
| 2011/0089942 | A1 | 4/2011 | Goodwill et al. |
| 2011/0098558 | A1 | 4/2011 | Weaver et al. |
| 2012/0094852 | A1 | 4/2012 | Berman et al. |
| 2013/0022969 | A1 | 1/2013 | Kim et al. |
| 2013/0063141 | A1 | 3/2013 | Hiltawsky et al. |
| 2013/0079623 | A1* | 3/2013 | Rueckert ............... A61B 5/055 |
| | | | 600/409 |
| 2014/0097829 | A1 | 4/2014 | Wang et al. |
| 2014/0322103 | A1 | 10/2014 | McDevitt et al. |
| 2015/0300987 | A1 | 10/2015 | Rahmer et al. |
| 2018/0242877 | A1 | 8/2018 | Kusakabe et al. |

FOREIGN PATENT DOCUMENTS

| | | |
|---|---|---|
| EP | 1262766 A2 | 12/2002 |
| WO | WO 2014/045811 A1 | 3/2014 |

OTHER PUBLICATIONS

Buguz, T., et al., "Magnetic Nanoparticles—Particle Science, Imaging Technology, and Clinical Applications," World Scientific Publishing (2010).
Cheng, M., et al., "Nanotechnologies for Biomolecular Detection and Medical Diagnostics," Curr. Opin. Chem. Biol. 10(1), 11-19 (2006).
De Haro, L., et al., "Magnetic relaxometry as applied to sensitive cancer detection and localization," Biomed. Eng.—Biomed. Tech., 60(5), 445-455 (2015).
Giljohann, D., et al., "Drivers of Biodiagnostic Development," Nature, 462(7272) 461-464 (2009).
Gleich, B., "Tomographic imaging using the nonlinear response of magnetic particles," Nature, 435(7046), 1214-1217 (2005).
Goodwill, P., et al., "Multidimensional X-Space Magnetic Particle Imaging," IEEE Trans Med Imaging, 30(9): 1581-1590 (2011).
Hall, D., et al., "GMR biosensor arrays—a system perspective," Biosens Bioelectron. 25(9), 2051-2057 (2010).
Hathaway, H.J., "Detection of breast cancer cells using targeted magnetic nanoparticles and ultra-sensitive magnetic field sensors," Breast Cancer Research, 13, R108 (2011).
Issadore, D., et al., "Magnetic sensing technology for molecular analyses," Lab Chip, 14(14), 2385-2397 (2014).
Knopp et al., "Magnetic Particle Imaging—An Introduction to Imaging Principles and Scanner Instrumentation," Springer Science & Business Media (2012).
Konkle J., "Magnetic Particle Imaging with Advanced Tomographic Reconstruction Methods," Ph.D Thesis, University of California, Berkeley (2014).
Kotitz, R., et al., "Determination of the binding reaction between avidin and biotin by relaxation measurements of magnetic nanoparticles," J. Magn. Magn. Mater., 194, 62-68 (1999).
Landry, G., et al., "Characterization of single magnetic particles with InAs quantum-well Hall devices," Appl. Phys. Lett., vol. 85, No. 20, pp. 4693-4695 (2004).
Lee, H., et al., "Recent Developments in Magnetic Diagnostic Systems," Chem. Rev., 115(19), 10690-10724 (2015).
Lemons, D., "Paul Langevin's 1908 paper 'On the Theory of Brownian Motion'," Am. J. Phys. 65, 1079 (1997).
Mákiranta, J., et al., "Magnetic relaxation switches capable of sensing molecular interactions," 28th Annual International Conference of the IEEE Engineering in Medicine and Biology Society, New York, USA, Conf Proc IEEE Eng Med Biol Soc., 4598-4601 (2006).
Mihajlovic, G., "Detection of single magnetic bead for biological applications using an InAs quantum-well micro-Hall sensor," Appl. Phys Lett., 87, 112502 (2005).
Noh, J., et al., "Biosensors in Microfluidic Chips," Top Curr. Chem., 304, 117-152 (2011).
Park, K., et al., "Multiplexed sensing based on Brownian relaxation of magnetic nanoparticles using a compact AC susceptometer," Nanotechnol., 22(8), 085501 (2011).
Perez, J. et al., "Magnetic relaxation switches capable of sensing molecular interactions," Nat Biotechnol., 20, 816-820 (2002).
Rahmer, J., et al., "3D Real-time Magnetic Particle Imaging: Encoding and Reconstruction Aspects," Proceedings of the First International Workshop on Magnetic Particle Imaging, pp. 126-131 (2014).
Rauwerdink, A., "Simultaneous quantification of multiple magnetic nanoparticles," Nanotechnology, 21(45), 455101 (2010).
Wang, R., et al., "Lateral Flow Immunoassay," Humana Press (2009).
Weizenecker, J., "Three dimensional real-time in vivo magnetic particle imaging," Phys. Med. Biol., 54(5), L1-L10 (2009).
Yu, E., et al., "Magnetic Particle Imaging: A Novel in Vivo Imaging Platform for Cancer Detection," Nano Lett. 17(3) 1648-1654 (2017).
Zheng, B., et al., "Quantitative Magnetic Particle Imaging Monitors the Transplantation, Biodistribution, and Clearance of Stem Cells in Vivo," Theranostics. 6 (3), 291-301 (2016).
Zhou, X., "First in vivo magnetic particle imaging of lung perfusion in rats," Phys. Med. Biol. 62(9), 3510-3522 (2017).
Kim et al., "Magnetic force-based multiplexed immunoassay using superparamagnetic nanoparticles in microfluidic channel," Lab on a Chip 5.6: 657-664 (Apr. 29, 2005).
Bhalla Nikhil et al., "Electrowetting enabled magnetic particle immunoassay with on-chip magnetic washing," 2013 IEEE Sensors, IEEE, pp. 1-4, XP032563316 (Nov. 3, 2013).
Kai Wu et al., "Magnetic nanoparticles in nanomedicine," arxiv.org, Cornell University Library, 201 Olin Library Cornell University Ithaca, NY 14853, XP081428907 (Nov. 4, 2018).
Knopp T. et al., "Limitation of measurement-based system functions inmagnetic particle imaging," Proceeding vol. 7626, Medical Imaging 2010: Biomedical applications in molecular, structural, and functional imaging, Mar. 9, 2010, pp. 76261F-1-76261F-8, XP040546981, abstract, Section 4, figure 2.
Timo F. Sattel et al, "Fast track communication; single-sided device for magnetic particle imaging," Journal of Physics D: Applied Physics, Institute of Physics Publishing, Bristol, GB, vol. 42, No. 2, Jan. 21, 2009, p. 22001, XP020149056, ISSN: 0022-3727, DOI: 10.10.

\* cited by examiner

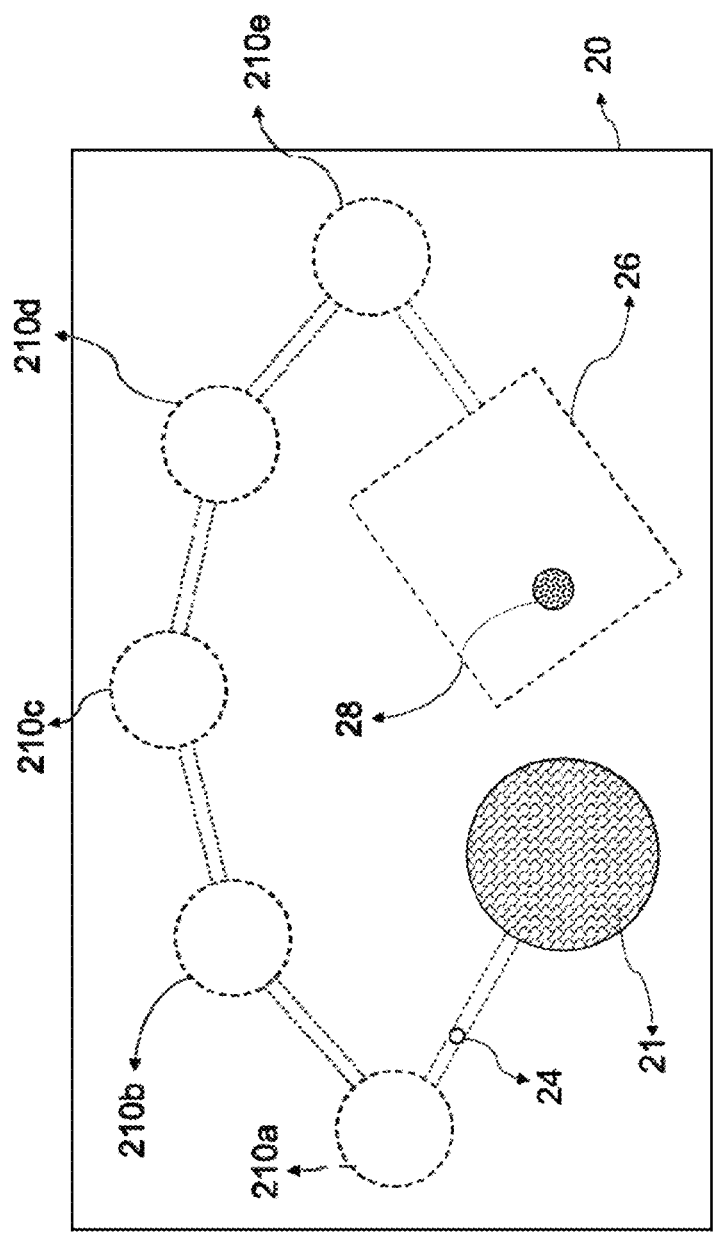

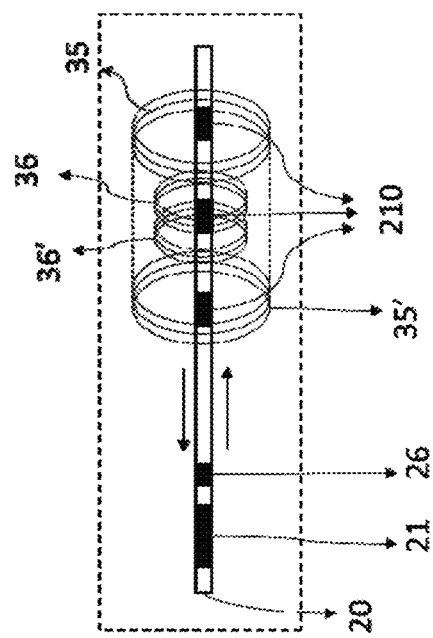
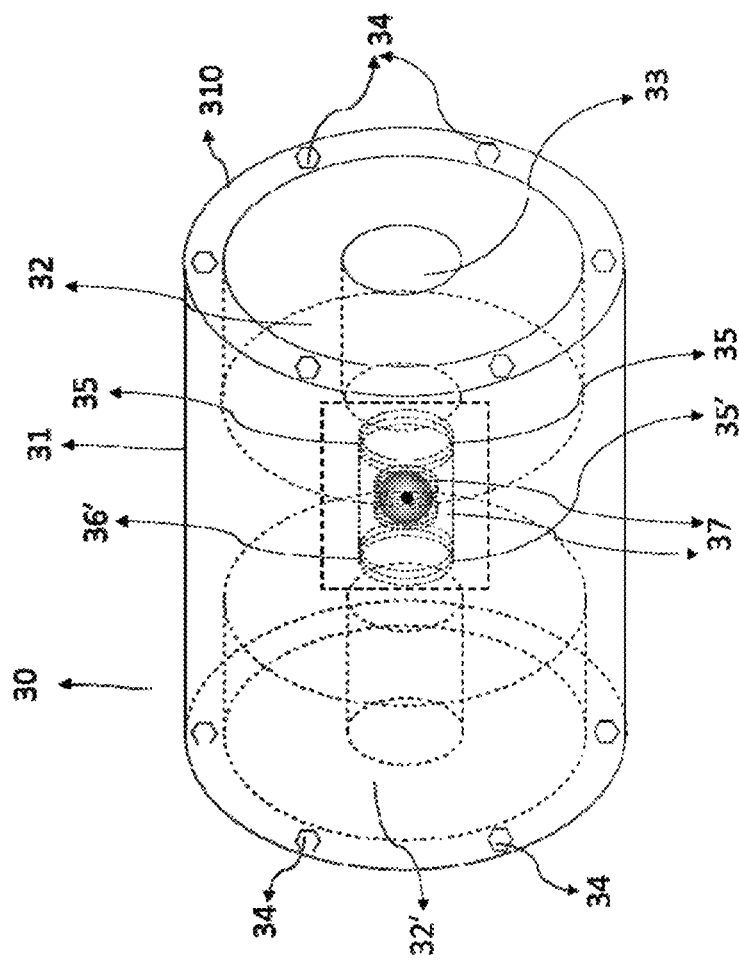
FIG. 10B
FIG. 10A

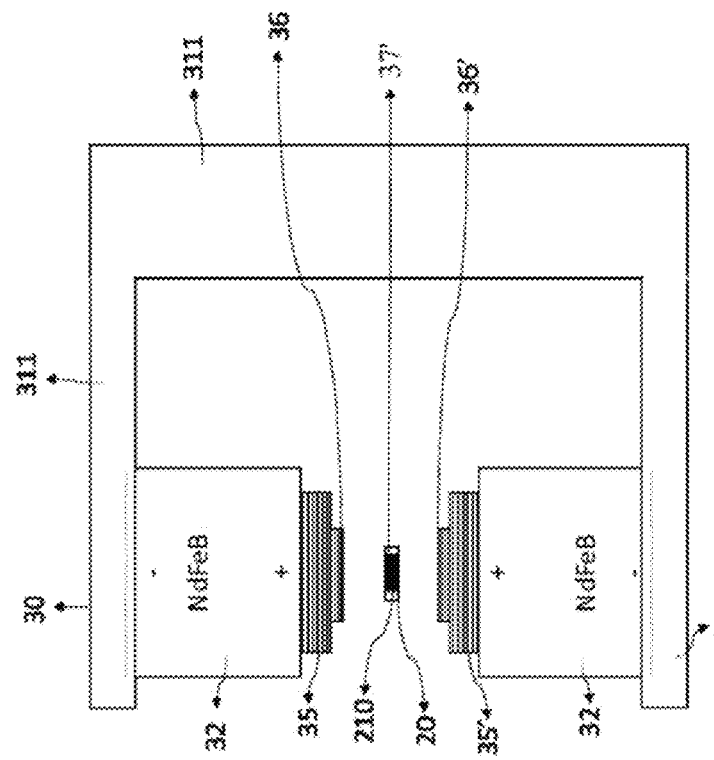
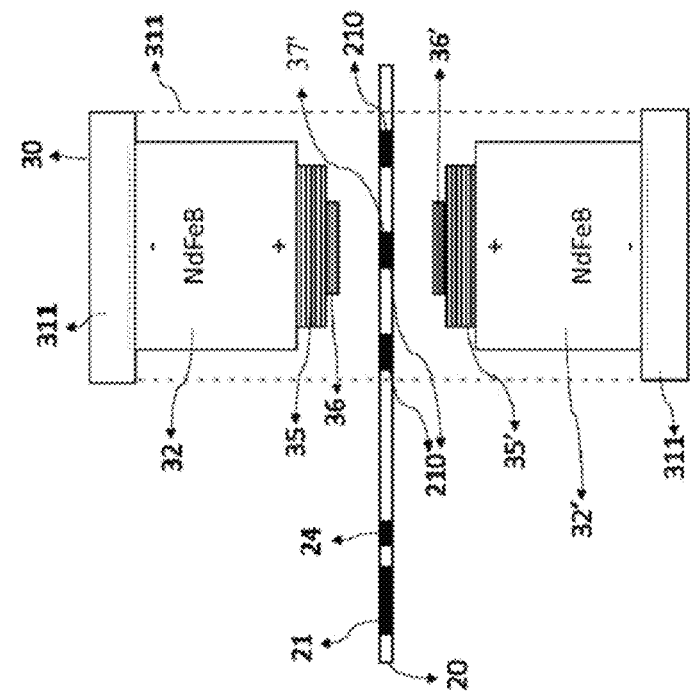

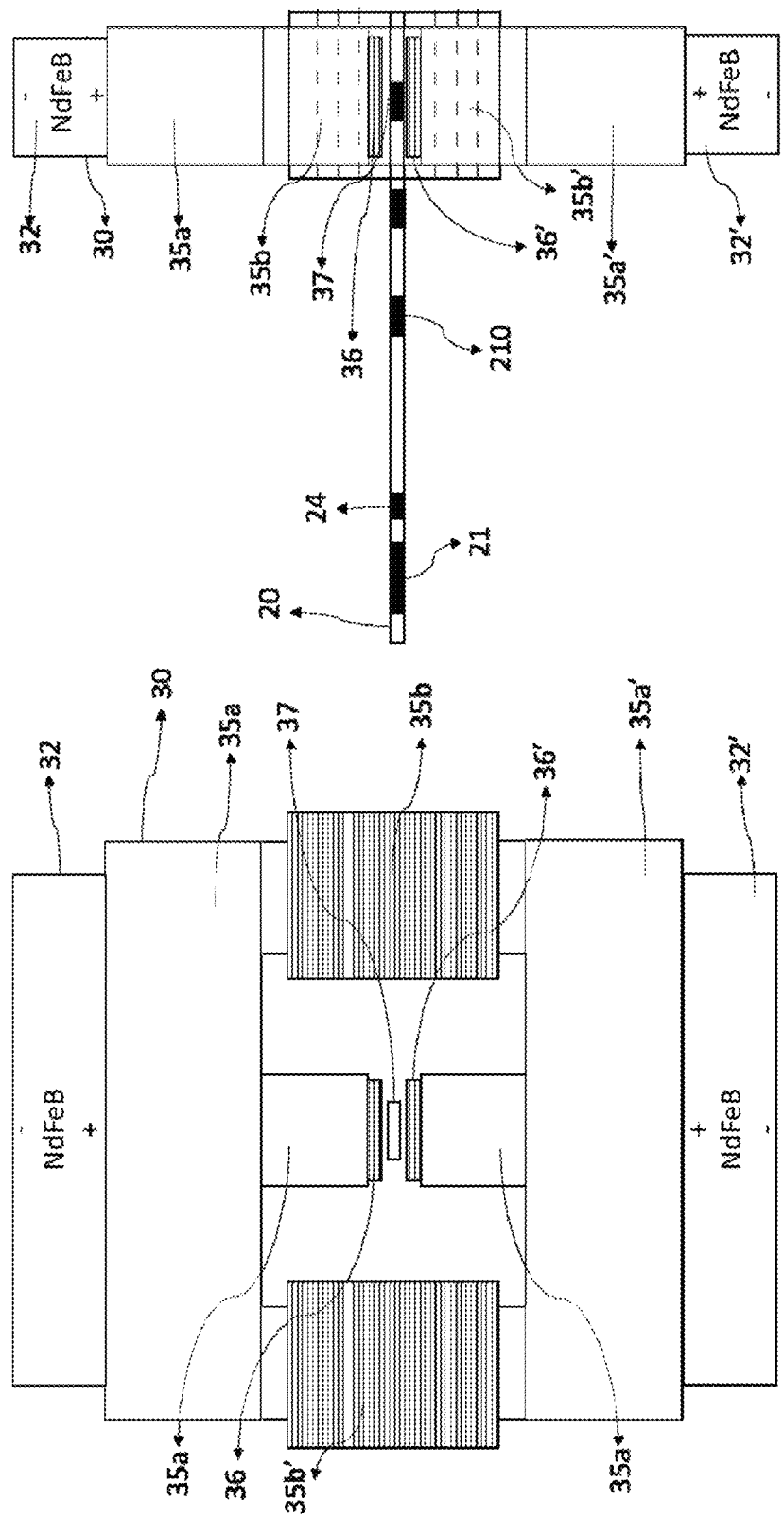

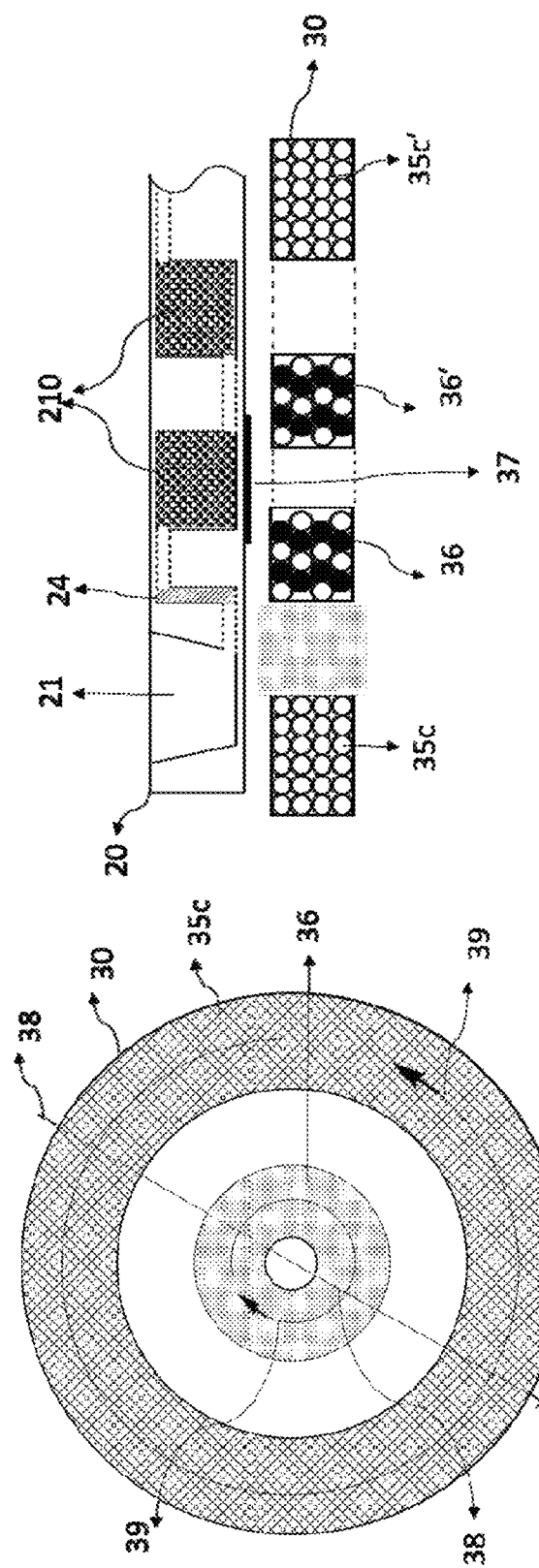

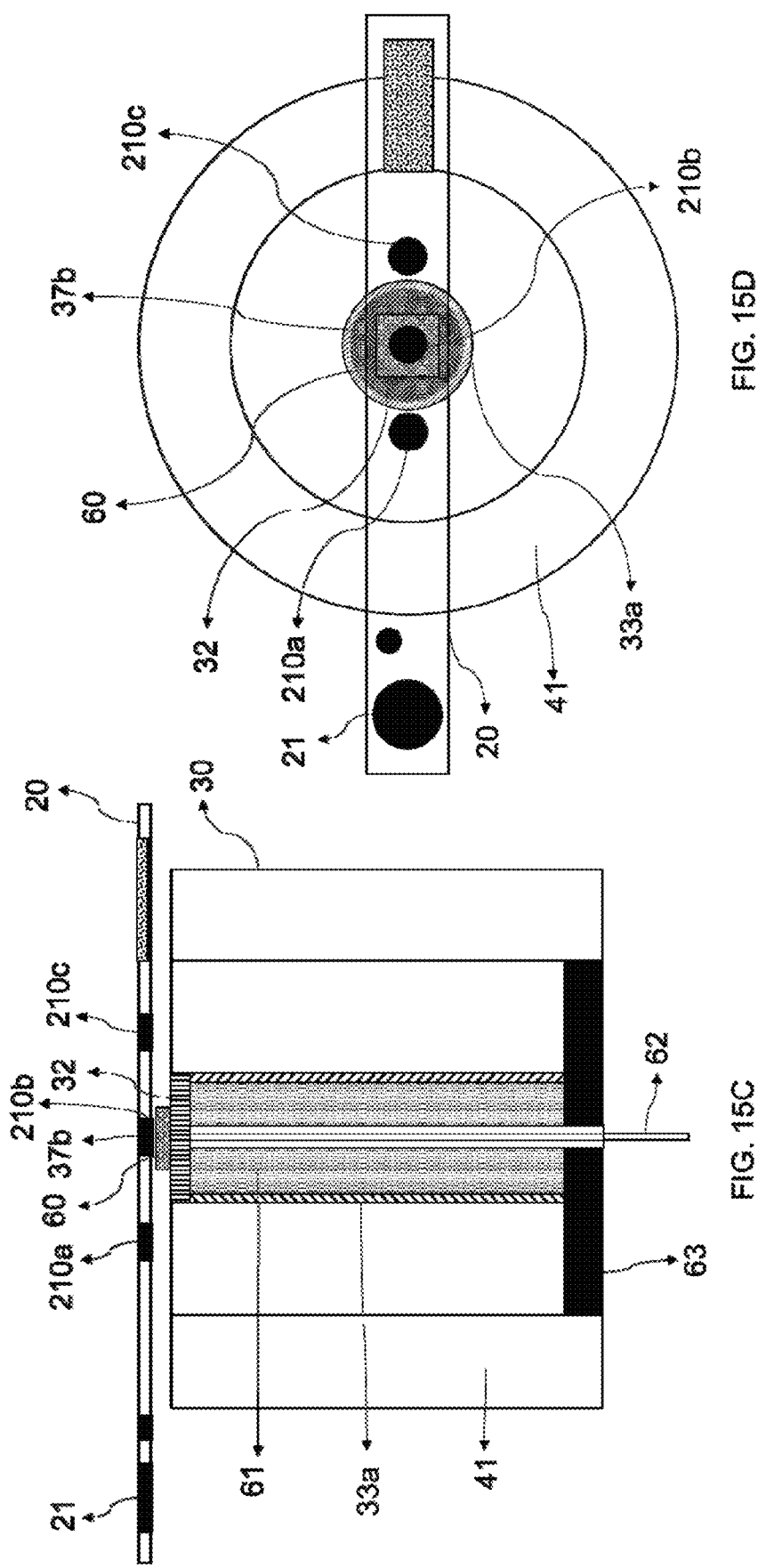

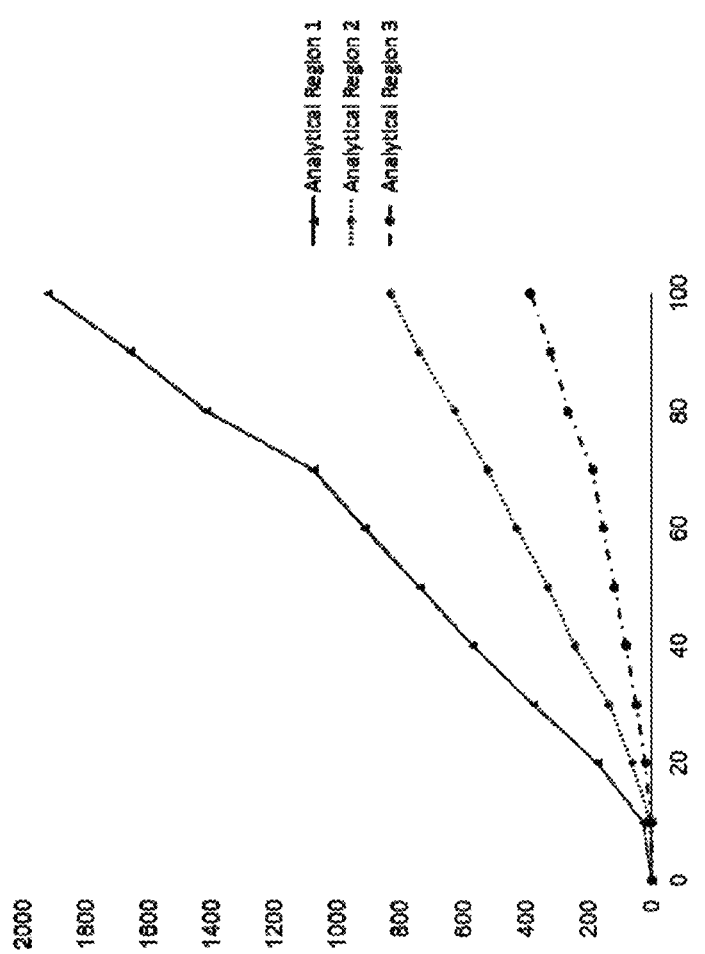

SUPERPARAMAGNETIC PARTICLE IMAGING AND ITS APPLICATIONS IN QUANTITATIVE MULTIPLEX STATIONARY PHASE DIAGNOSTIC ASSAYS

CROSS-REFERENCE TO RELATED APPLICATIONS

The subject application claims priority on U.S. provisional application Nos. 62/655,828 filed on Apr. 11, 2018 and 62/664,946 filed on May 1, 2018. The subject matters and contents of both U.S. provisional applications are incorporated herein by reference.

TECHNICAL FIELD

The present invention relates to biosensing technology, particularly, analytical method and chips and devices used therein that simultaneously measure multiple analytes in a sample using the super-paramagnetic particle imaging or other technologies.

BACKGROUND OF INVENTION

Biosensing refers to any approach to detect biological elements and associated software or computer technologies that identify biological characteristics of a sample and has become an essential part of medical diagnostics, environmental monitoring, and food safety assurance. Biosensing systems incorporate electrical, electronic, and photonic devices with biological materials (such as tissue, enzymes, and nucleic acids) and chemical analysis to produce detectable signals for monitoring or identifying biological phenomena. Biosensing has been increasingly applied in biomedicine, food production and processing, and detection of bacteria, viruses, and biological toxins for bio-warfare defense and represents remarkable convergence of advanced bio-, nano-, and info-technologies in a totally new scientific paradigm.

Biosensing technology may be categorized into optical, electro-chemical, and magnetic biosensing. First, based on optical transduction mechanisms, optical biosensing is categorized into luminescence methods, including fluorescence, phosphorescence, fluorescence resonance energy transfer (FRET), chemiluminescence, bioluminescence, quantum dots, absorbance, and scattering; and surface methods, including surface plasmon resonance (SPR), surface-enhanced Raman scattering (SERS), and interference. Generally, the optical biosensing methods are sensitive and readily multiplexed.

Second, electrochemical biosensing includes methods using enzyme-linked assays, field-effect sensors, electroactive tag, nanoparticle-based sensors, and electrochemiluminescence-based sensors. These methods and assays are intrinsically interfacial where biological recognition or physical changes that follow from a recognition event directly change the electrical properties of a contacting material. These assays are simple, sensitive, and have enhanced discrimination between the specific analyte and background analyte due to localization of binding events to the interface. Additionally, these assays are compatible with extension to array formats and integration with microfluidic structures.

Third, magnetic biosensing generally includes methods based on AC susceptometry, Hall effect measurements, giant magnetoresistance, superconducting quantum interference devices, and magnetic inductance. Compared with optical and magnetic biosensing methods, magnetic particle-based sensing methods has improved biocompatibility, environmentally safety, and lower cost to synthesize. Moreover, magnetic particle-based sensing methods provide less background noise, because there is little or no magnetic signal from biological samples. Hence, they have received considerable attention for developing biosensing and diagnostic tools. See Issadore, D., et al, "Magnetic sensing technology for molecular analyses," Lab Chip, 14(14), 2385-2397 (2014).

AC magnetic susceptometry is a precise detection technique that capitalizes on the diffusive properties of magnetic nanoparticles (MNPs) in solution. See Park, K., et al, "Multiplexed sensing based on Brownian relaxation of magnetic nanoparticles using a compact AC susceptometer," Nanotechnol, 22(8), 085501 (2011). The technique is based on the principle of a Brownian relaxation detection scheme that uses the random rotational motion of magnetically tagged sensors determined via measurement of collective magnetic susceptibility as a function of the frequency of the applied magnetic field. When the excitation frequency is close to the rotational motion frequency of the magnetically labeled sensor, a large increase in the loss component of the complex magnetic susceptibility occurs. The phenomenon is observed as a peak frequency of the imaginary component of the complex magnetic susceptibility (90° out-of-phase: $\chi''$). The application of the technique for biological diagnostics relies on a shift in the peak frequency of $\chi''$ upon target binding to labeled MNPs. If a target molecule then binds to a specified receptor on the sensor, the hydrodynamic size of the sensor is effectively increased and there is a readily measurable shift of the frequency maximum to lower values with cubic dependence on hydrodynamic radius. AC susceptometer exhibits high sensitivity in magnetic fields as low as 10 pT for 1 mg/ml concentration and 5 µl volume, however, the application of the method is limited to solution media.

Hall sensors based on the Hall effect measurement are defined as a cross shape with an arm width w of roughly 1 µm by photolithography and dry etch with an argon ion mill. See Mihajlovic, G, "Detection of single magnetic bead for biological applications using an InAs quantum-well micro-Hall sensor," Appl. Phys Lett., 87, 112502 (2005); and Landry, G., et al., "Characterization of single magnetic particles with InAs quantum-well Hall devices," Appl. Phys. Lett., 85, 4693 (2004). Some crosses are further defined with focused ion beam milling to have arm widths of 500, 600, and 700 nm. Each sensor is characterized using van der Pauw and Hall measurements. After processing, values of the Hall coefficient and sheet resistance are in the range of $0.031 < R_H < 0.046 \Omega/Oe$ and $150 < R_H < 600 \Omega/Oe$, respectively. When a sensor chip is placed in a perpendicular AC excitation magnetic field $\tilde{B}_0$ that varies at frequency $f_0$, the sensor is biased by a DC current $I_0$, and the Hall voltage is measured at the frequency $f_0$ with a lock-in amplifier. Since the bead is superparamagnetic, its magnetization follows Langevin behavior. The AC signal essentially measures the slope of the Langevin curve, hence depends on the DC magnetic state of the bead. Therefore, when the bead is exposed to a DC magnetic field $B_1$, its magnetic state shifts towards lower susceptibility and it lowers the induced AC magnetization in the bead, which reduces average AC stray field from the bead sensed by the cross and manifests itself as a drop in the AC Hall voltage signal. The linearity of the Hall sensors ensures that $B_1$ does not induce any change in the AC Hall signal on an empty Hall cross without a bead on top. The drop is, therefore, a definitive signal indicating the presence of a bead on the Hall cross. The weakness of the method is the large offset created by the direct sensor Hall response to the AC excitation field which is typically orders of magnitude larger than the small signal from the magnetic bead.

Giant magnetoresistance (GMR) is a quantum mechanical magnetoresistance effect observed in multilayers composed of alternating ferromagnetic and non-magnetic conductive layers. See Hall, D., et al., "GMR biosensor arrays—a system perspective," Biosens Bioelectron. 25(9), 2051-2057 (2010); and Baselt, D., "A biosensor based on magnetoresistance technology," Biosens Bioelectron, 13, 731-739 (1998). The effect is observed as a significant change in the electrical resistance depending on whether the magnetization of adjacent ferromagnetic layers is in a parallel or an antiparallel alignment. The overall resistance is relatively low for parallel alignment and relatively high for antiparallel alignment. The magnetization direction can be controlled, for example, by applying an external magnetic field. The effect is based on the dependence of electron scattering on the spin orientation. The developments in magnetoresistive materials have made it possible to photopattern highly-sensitive micrometer-scale magnetic field sensors. Magnetoresistive materials are typically thin-film metal multilayers, the resistance of which changes in response to magnetic fields. Several fundamentally different varieties have been described, including anisotropic magnetoresistive and giant magnetoresistive materials. Magnetoresistive sensors are used commercially for reading magnetic tapes or disks, for hand-held magnetic field sensors, and for position transducers. Using magnetoresistive materials, a microfabricated detector for magnetic bead assays can be built. Such a detector can be embedded in the assay substrate and would detect the beads in its own immediate vicinity. The primary advantage of this approach over optical or micromechanical detection is that thousands of detectors can be fabricated on a single chip measuring about 1 cm on a side. The GMR sensors suffered from its non-linearity and monolayer nature. It's very sensitive to the surface of the objects and the distance of the magnetic beads and the sensor.

Superconducting quantum interference devices (SQUIDs) are very sensitive magnetometers used to measure extremely subtle magnetic fields, based on superconducting loops containing Josephson junctions. See Kotitz, R., et al., "Determination of the binding reaction between avidin and biotin by relaxation measurements of magnetic nanoparticles," J. Magn. Magn. Mater., 194, 62-68 (1999); Hathaway HJ, "Detection of breast cancer cells using targeted magnetic nanoparticles and ultra-sensitive magnetic field sensors," Breast Cancer Research, 13, R108 (2011); De Haroa, L., et al., "Magnetic relaxometry as applied to sensitive cancer detection and localization," Biomed. Eng.-Biomed. Tech., 60(5), 445-455 (2015); and Perez, J., et al., "Magnetic relaxation switches capable of sensing molecular interactions," Nat Biotechnol., 20, 816-820 (2002). SQUIDs are sensitive enough to measure fields as low as 5 aT ($5 \times 10^{-18}$ T) with a few days of averaged measurements. Their noise levels are as low as 3 fT Hz-½. For comparison, a typical refrigerator magnet produces 0.01 tesla ($10^{-2}$ T), and some processes in animals produce very small magnetic fields between $10^{-9}$ T and $10^{-6}$ T. There are two main types of SQUIDs: direct current (DC) and radio frequency (RF). RF SQUIDs can work with only one Josephson junction (superconducting tunnel junction). While SQUIDs are very sensitive, they require cryogenic condition and expensive equipment and are not suitable for routine analysis.

Magnetic inductance refers to the phenomenon that when magnetic particles pass coils, they change the inductance of the coils due to the change in relative permeability. See Miikiranta, J., et al., "Magnetic relaxation switches capable of sensing molecular interactions," 28th Annual International Conference of the IEEE Engineering in Medicine and Biology Society, New York, USA, Conf Proc IEEE Eng Med Biol Soc., 4598-4601 (2006). The change of inductance can be used to quantify the quantity of magnetic particles entering the coils. The method has been used in a number of devices for in vitro diagnostics, however, the method is not capable of multiplexing and has poor reproducibility.

Magnetic particle imaging (MPI) is an emerging non-invasive and highly sensitive tomographic technique as disclosed in U.S. Pat. No. 7,778,681B2. The first prototype of an MPI scanning device is disclosed in Gleich, B., "Tomographic imaging using the nonlinear response of magnetic particles," Nature, 435(7046), 1214-1217 (2005). MPI uses the non-linear response of magnetic particles to the changing external magnetic field, and its basic theory is the Langevin theory first devised by Paul Langevin in 1908 (Lemons, D., "Paul Langevin's 1908 paper 'On the Theory of Brownian Motion'," Am. J. Phys. 65, 1079 (1997)). It is disclosed that signals generated by magnetization of magnetic particles (tracer) in an alternating magnetic field are spatially encoded, and by linking the signals that are directly proportional to the concentration of the tracers and their location, a phantom is successfully imaged after reconstruction of the spatially encoded signals. The primary applications of MPI are in vivo imaging (Weizenecker, J., "Three dimensional real-time in vivo magnetic particle imaging," Phys. Med. Biol., 54(5), L1-L10 (2009); and Zhou, X., First in vivo magnetic particle imaging of lung perfusion in rats," Phys. Med. Biol. 62(9), 3510-3522 (2017)), cancer diagnosis (Yu, E., et al., "Magnetic Particle Imaging: A Novel in Vivo Imaging Platform for Cancer Detection," Nano Lett. 17(3) 1648-1654 (2017)); and cell tracking (Zheng, B., et al., "Quantitative Magnetic Particle Imaging Monitors the Transplantation, Biodistribution, and Clearance of Stem Cells In Vivo," Theranostics. 6 (3), 291-301 (2016)). The principle of the MPI and methods to construct a generic MPI instrument has been described in great details in Knopp et al., "Magnetic Particle Imaging—An Introduction to Imaging Principles and Scanner Instrumentation," Springer Science & Business Media (2012); and Buguz, T., et al., "Magnetic Nanoparticles-Particle Science, Imaging Technology, and Clinical Applications," World Scientific Publishing (2010).

Magnetic biosensing methods and techniques offer many advantages such as less interferents as human samples are naturally devoid of ferromagnetic materials (unlike electrical and optical technologies where interferents abound). MNPs have been used in biomedical separation technologies and for imaging. See Lee, H., et al., "Recent Developments in Magnetic Diagnostic Systems," Chem. Rev., 115(19), 10690-10724 (2015) for detailed discussion on the advantages and disadvantages of the current magnetic biosensing. Up to now, existing magnetic sensing methods used in diagnostics suffers a major drawback of the lack of capability to concurrently measure multiple analytes, unlike the optical sensing methods; another issue that the magnetic sensing methods face is that they often deal with homogenous media or monolayer.

In recent years, as clinical need increases, different point of care (POC) sensing methods have enjoyed explosive growth. See Cheng, M., et al., "Nanotechnologies for Biomolecular Detection and Medical Diagnostics," Curr. Opin.

Chem. Biol. 10(1), 11-19 (2006); and Giljohann, D., et al., "Drivers of Biodiagnostic Development," Nature, 462 (7272) 461-464 (2009). These point of care methods are often based on electrical impedance, colorimetric, optical, and magnetic sensing strategies, and they face many challenges, particularly for cellular, molecular, and genetic testing, including further improving sensitivity and specificity, increasing complexity of tests, needs for complicated upfront purification (and possible loss of precious samples), unique issues associated with low volume testing, higher training needs, higher quality control costs, regulatory burden, and expense.

Lateral flow immunoassay (LFIA) is one of the most widely used formats in the point of care devices. Lateral flow immunoassay uses porous membranes, antibodies (monoclonal and/or polyclonal), and usually a visible signal generating system to produce sensitive, disposable, and easy-to-use tests. The technology has been used in rapid diagnostic tests for pregnancy, fertility, drugs of abuse, and infectious disease as well as DNA detection. Similar tests are available both over-the-counter and at point-of-care. They are easy to use and inexpensive to make, making it one of the most widely used format in point of care assays. However, due to its design and construction, LFIAs have inefficient sample conjugation, poor connection between sections, inconsistent membranes, leakage of samples, variable capturing region, and more (Wang, R., et al., "Lateral Flow Immunoassay," Humana Press, 2009). These issues result in large coefficient of variation (CV) and limit LFIA largely to qualitative assays. The large coefficient of variations in the LFIA are primarily due to the poor connection between sections, inconsistency of the membrane used to immobilize the capturing materials and transport the samples, leakage of samples through the edge of the strips, variable capturing material striped in the analytical region. The manual readout is often ambiguous.

A microfluidics is another widely used format in the point of care devices. A microfluidic chip is a pattern of microchannels, molded or engraved. Fluids in the microchannels are directed, mixed, separated, or manipulated to attain multiplexing, automation, and high-throughput systems. The microchannel network design must be precisely elaborated to achieve desired features such as lab-on-a-chip, detection of pathogens, electrophoresis, DNA analysis etc. Microfluidic technology for chemical or bioanalytical purposes has reduced reagent consumption, short analysis time, a small-sized scale, versatility, and high sensitivity. Over the last three decades, microfluidics-based miniaturized analytical systems and techniques for chemical analysis, bioanalysis, and clinical diagnostics have enjoyed explosive growth. However, use of microfluidics for chemical and biological analysis involves considerable challenges such as complicated stringent pretreatment and handling of the samples and difficulty and complication to design and manufacture. The analytes measured in microfluidic chips are usually in solution, limiting the method to be used in detecting the analytes and the cost and complexity to develop and manufacture (Noh, J., et al., Top. Curr. Chem., 304, 117-152 (2011)). Due to the complexities, they often need external driving force to complete the process and tend to be more expensive.

ELISA format is less frequently used in the point of care devices. Enzyme-linked immunosorbent assay (ELISA) is a plate-based assay technique designed for detecting and quantifying substances such as peptides, proteins, antibodies and hormones. In an ELISA, an antigen must be immobilized on a solid surface and then complexed with an antibody that is linked to an enzyme. Detection is accomplished by assessing the conjugated enzyme activity via incubation with a substrate to produce a measurable product. The most crucial element of the detection strategy is a highly specific antibody-antigen interaction. The limitations of ELISA format are multi-steps operation, difficult reagent handling, and larger equipment. It's not suited for point of care applications. Due to the limitations of the format, ELISA is often used in large clinical analyzers, but not in point of care devices, despite of its high sensitivity and specificity.

Construction and design of a disposable and bio-degradable assay format are usually limited by kinds and forms of the sample to be analyzed. Constraints are imposed by the analytical environment, the analytes, materials, physics of the analytical method used for measurement and not the least, the technology used to manufacture devices at scale, all of which are driven by market price, competition, and performance.

Most point of care devices are linear in form. For example, common plastic cassettes are used to hold LFTs such as an Early Pregnancy Test (EPT). These are constructed of a backing card, a lateral flow membrane (nitrocellulose) and varying arrangements of sample introduction pads, filters and absorption membranes. A plastic case of several familiar designs holds the components so that they are convenient to apply a liquid sample, develop and then to read the results. One of the newest issues in the use of these kinds of tests is the disposal of the used test devices. In the last 2 years, over 650 million assays were performed for malaria, HIV, dengue fever in the African continent alone. It has become an issues in developing countries with limited capacity of dealing with biological waste. Devices made out of biodegradable materials are highly desirable.

SUMMARY OF THE INVENTION

The present invention combines superparamagnetic particle imaging technology and hybrid point of care (HY-POC) chip to provide a solution to all the problems while retaining and expanding the advantages of magnetic biosensing technologies. Further, the hybrid point of care chip of the present invention not only solves the problems of the existing formats but also takes the full advantages of the superparamagnetic particle imaging technology. Moreover, the present invention provides an analyzer device to be used in connection with the analytic method and chips.

The superparamagnetic nanoparticle-based analytical method of the present invention comprises providing a sample comprising at least one or more analytes in a sample matrix, providing a point of care chip having at least one or more analytical regions, each of the analytical regions is a stationary phase having at least one or more sections, labeling each of the analytes in the sample with a superparamagnetic nanoparticle and immobilizing the labeled analytes in the stationary phase, providing an analytical device having a means for exciting the superparamagnetic nanoparticles in vitro and a means for sensing, receiving, and transmitting response of the excited superparamagnetic nanoparticles, placing the point of care chip with the analytic region comprising the stationary phase in the analytical device and exciting the superparamagnetic nanoparticles in vitro, sensing, receiving, and transmitting the response of the superparamagnetic nanoparticles, and analyzing the response of the superparamagnetic nanoparticle and determining characteristic of the analytes, wherein the response of the superparamagnetic nanoparticles comprises harmonics.

In the present invention, the superparamagnetic nanoparticle-based analytical method may further comprises providing a changing external magnetic field in the analyzer and a field free zone, which can be a field free point, or field free line, or field free space, within the changing external magnetic filed, and placing the point of care chip in the analyzer, the field free zone scans the entire analytical region, and excitation coils excite the superparamagnetic nanoparticles on stationary phase in the field free zone to generate the spatially encoded response, wherein the stationary phase of the analytical region comprises two or more sections, superparamagnetic nanoparticles in the sections generate spatially encoded response, and the characteristics of the analytes are determined quantitatively from the spatially encoded response with or without removing unbound analytes or reconstruction.

In the present invention, the number of sections in the stationary phase is in a range of 1 to 20, and preferably, the stationary phase consists of one single section.

In the present invention, each of the stationary phases may be adopted to immobilize at least one or more different superparamagnetic nanoparticles in a range of 1 to 20.

In the present invention, each of the superparamagnetic nanoparticles may correspond to each of the labeled analytes and be distinct from other superparamagnetic nanoparticles on the labeled analytes in the sample matrix.

In the present invention, the superparamagnetic nanoparticle may have a particle size in a range of 1 nm to 1000 nm. The superparamagnetic nanoparticle may be made of a material that is Fe, CoFe, Co, Co alloy, ferrite, cobalt nitride, cobalt oxide, Co—Pd, Co—Pt, iron, iron alloy, Fe—Au, Fe—Cr, Fe—N, FeO, Fe—Pd, Fe—Pt, Fe—Zr—Nb—B, Mn—N, Nd—Fe—B, Nd—Fe—B—Nb—Cu, Ni, or Ni alloys. Further, the superparamagnetic nanoparticle may be in a spherical, elliptical, tabular, or tubular shape, and may be coated with a material that alters response of the superparamagnetic nanoparticle to the external magnetic field.

In the present invention, the sample is in a sample matrix that may be a liquid, an extract of a solid, a liquid or air sample, or a mixture thereof. Further, the sample matrix may be whole blood, serum, plasma, urine, saliva, feces, tears, or sweat.

In the present invention, the analyte may be an organic molecule, a biological molecule, a peptide, a polymer, an amino acid, a protein, an enzyme, an antibody, a DNA, an RNA, a virus, a cell, a germ, a pathogen, an inorganic molecule, a drug, or a mixture thereof.

In the present invention, the analytical region may be in an assay format that is hybrid point of care, lateral flow, microfluidic bead, or ELISA monolayer.

The present invention further provides a 3-dimensional hybrid point of care chip that comprises at least one or more sample introduction region, at least one or more analytical regions, fluid absorption area, and optionally, a reagent reservoir. The structure of the 3-dimensional point of care chip is a laminate having a number of levels in a range of 1 to 10, and sample introduction regions, the reagent reservoir, the analytical regions, and the fluid absorption area are sequentially connected by microchannels that allow a sample comprising an analyte to be divided and directed to the levels of the laminate.

In the present invention, the 3-dimentional point of care chip may further comprise a switching column when the laminate has two or more levels, and the switching column is positioned between the sample introduction region and the analytical region and connects the levels of the laminate to allow the sample comprising the analyte to be divided and directed to different levels of the laminate.

In the present invention, the 3-dimentional hybrid point of care chip may further comprise a liquid driving mechanism, such as a diaphragm pump connected to the sample introduction region.

In the present invention, at least one or more levels of the laminate are laminating layers of films for the sample comprising the analyte to flow therein, and surface of the films are optionally modified. The films are made of a material that is plastic, adhesive, paper, wood, fiber, silicon, polydimethylsiloxane (PDMS), poly(methyl methacrylate) (PMMA), fiberglass, cellulose, polysaccharide, protein polymer, or calendared particles.

In the present invention, the number of the sample introduction regions may be in a range of 1 to 5. The sample introduction region may further comprise an erythrocyte cell separation mechanism such as a device described by Aunet (U.S. Pat. No. 4,933,092 to Aunet, D., 1990). Further, the sample introduction region may comprise the labeled analyte recognition materials and/or reagents that help sample to flow in the microchannels, control the pH of the sample, and enhance the reaction between analytes and recognition materials or capturing materials in analytical regions. Generally, the sample introduction region may hold a sample at a volume in a range of 1 to 200 micro liter, and the sample may be whole blood, plasma, serum, urine, saliva, tears, sweat, feces extract, DNA/RNA extract, a solution containing antigen, antibody, enzyme, protein, peptide, amino acid, hormone, organic molecule, inorganic molecule, biomarker, industrial contaminant, pathogen, virus, cell, cell culture extract, or environmental sample.

In the present invention, the number of the switching columns in the chip may be in a range of 1 to 5.

In the present invention, the number of the reagent reservoirs in the chip may be in a range of 0 to 10. The reagent reservoir may be for containing a reagent or reagents necessary for recognizing and immobilizing the analyte in the sample.

In the present invention, the number of the analytical regions in the chip may be in a range of 1 to 20. The analytical region is a stationary phase that comprise one or more sections that are assembled together, the number of the sections in the analytical region is in a range of 1-20, and each section is in a form of particle, pore membrane, water insoluble gel, or colloid. The particle of the stationary phase may be made of plastic, silica, glass, alumina, organic polymer, inorganic polymer, or biodegradable polymer.

In the present invention, the pore membrane may be constructed out of plastic, fiber, polymer, polysaccharide, cellulose, paper, wood, biological construction, biological scaffold, fiber glass, biodegradable polymer, or protein polymer, and the pore membrane is woven, non-woven, or of calendared particles.

In the present invention, the stationary phase may be functionalized by physical adsorption or covalent bonding with a recognition reagent specific to the analyte in the sample.

In the present invention, the stationary phase may be pre-formed to a suitable shape and size for directly placing or dispensing into the analytical region. And the analytical region may be constructed within one level, or across multiple levels of the laminate.

In the present invention, the number of the fluid absorption areas in the chip is in a range of 1 to 5. The fluid absorption area may comprise a chamber with fluid absorption pads. The fluid absorption pads may be made of hydrogel, particles, calendared particles, or pores membranes, and the pore membranes may be constructed out of plastic, fiber, polymer, polysaccharide, cellulose, paper, wood, biological constructions, biological scaffold, fiber glass, biodegradable polymer, or protein polymer.

The present invention also provides an analytical method using the hybrid point of care chip of the present invention, comprising recognizing the analyte in the sample by the reagent in the reagent reservoir, immobilizing the recognized analyte in the analytical region, and determining a characteristic of the analyte by a detection method that is a magnetic, acoustic, radioactive, fluorescent, chemiluminescent detection method, or a combination thereof. The reagent may comprise magnetic particles, fluorescent particles, chemiluminescent particles, radioactive particles, or a mixture thereof, that are functionalized with antibody, protein, DNA/RNA probe, or chelating reagent; the magnetic, fluorescent, chemiluminescent, or radioactive labeled antibody, protein, DNA/RNA probe, or chelating reagent bind to and recognize the analyte in the sample; the reagent is directly placed in the reagent reservoir or absorbed onto a solid support and placed in the reagent reservoir, and the analytical region has sections of stationary phases that are functionalized with recognition reagents that immobilize the recognized analytes.

In the present invention, the hybrid point of care chip may have a plurality of the analytical regions that are arranged along a circular arc. The plurality of the hybrid point of care chips are arranged to form an array and share a same sample introduction region.

In the present invention, the hybrid point of care chip is designed to run the sample automatically without any external assistance through capillary effect.

In the present invention, the magnetic detection method may include superparamagnetic imaging, total accumulation of magnetic particle, magnetic inductance, AC magnetic susceptometry, Complementary metal-oxide-semiconductor (CMOS) AC susceptometry, Hall effect, magnetoresistance, giant magnetoresistance (GMR), colossal magnetoresistance (CMR), superconducting quantum interference devices (SQUIDs), magnetic relaxometry, or magnetic resonance imaging (MRI) spin relaxation times.

The present invention further provides a superparamagnetic particle imaging analyzer comprising a housing being placed along a horizontal axis and having an interior volume, a pair of permanent magnets fitted inside the interior volume of the housing along the horizontal axis, and each of the permanent magnets being held with a matching magnetic pole facing each other to create a field free region therebetween, a pair of excitation coils being placed along on the horizontal axis between the pair of the permanent magnets, each of the excitation coils being close to the field free region for creating alternate current in the field free region, and a pair of receive coils being placed along the horizontal axis between the pair of the excitation coils, each of the receive coils being close to the field free region. A sample with superparamagnetic nano particle labeled analyte immobilized in an analytical region is placed inside the interior volume of the housing and pass through the field free region where the superparamagnetic nano particles are excited and send out paramagnetic response that is sensed and transmitted by the pair of receive coils for analysis.

In the present invention, the permanent magnet may be made of NdFeB.

In one embodiment of the analyzer of the present invention, the housing is a cylinder and the interior volume is a cylindrical interior volume, the pair of the permanent magnets are in cylindrical shape and fit in the cylindrical interior volume of the housing, the pair of excitation coils are AC modulation field coils that form alternating current inside the field free region to excite the superparamagnetic nano particles, and the sample is on a hybrid point of care chip that moves co-linearly inside the cylindrical interior volume of the cylinder housing.

In another embodiment of the analyzer of the present invention, the housing is an open-sided C-shape frame, the pair of the permanent magnets are rectilinear in shape with positive pole of each of the permanent magnets being forced to face each other to create a rectilinear field free region, the pair of excitation coils are Helmholtz pair of coils to excite the superparamagnetic nano particles, and the sample containing immobilized superparamagnetic nano particle labeled analyte moves in from multiple directions into the linear field free region inside the housing.

In yet another embodiment of the analyzer of the present invention, the pair of the excitation coils are a pair of sintered Iron ferrite cores in a shape of an E and facing each other and being separated by an insulator, each leg of the E-shaped cores has solenoid coil winding to produce a field on the 2 diametrically opposed poles of the E-shaped cores that are shorted to form a gap, the pair of permanent magnets are forced with facing mutual positive poles to produce the field free region within the gap, and the sample is moved through the gap and accessible region for excitation and analysis.

In yet another embodiment of the analyzer of the present invention, the analyzer is a single-sided analyzer without the permanent magnets and comprising two concentrically placed transmit coils and receive coil. Currents in the two transmit coils are in opposite directions and form field lines with a field free region symmetrical to the field lines, the sample having the superparamagnetic nanoparticle labeled analytes are placed in the field free region for excitation, and the paramagnetic response of the superparamagnetic nanoparticle are sensed and transmitted by the receive coil.

In yet another embodiment of the analyzer of the present invention, the analyzer is a Hall sensor analyzer comprising a non-magnetizable hollow shaft, a permanent magnet in a shape of a cylinder, having a cylindrical interior inside, and being mounted and supported by the non-magnetizable hollow shaft therethrough, and a Hall sensor having bias leads and signals and being placed in the cylindrical interior of the permanent magnet and onto the non-magnetizable hollow shaft. In the embodiment, the permanent magnet has theoretical lines of magnetic force to create a magnetic force field, wherein the lines of magnetic force leaving the cylindrical permanent magnet create a null region at center of the cylinder and of the magnetic force fields. The permanent magnet provides induction to the sample having the superparamagnetic nanoparticle labeled analyte in the null region. The Hall sensor is placed in the null region at the center of the cylindrical interior, senses and receive the paramagnetic response of the superparamagnetic nanoparticles, and the bias leads and signals of the paramagnetic response are sent out for signal processing.

Further, the samples may be on a hybrid point of care chip comprising a plurality of analytical regions for samples and the analytical regions are arranged along a circular arc on the chip. In the present invention, the hybrid point of care chip with the configuration of the multiple analytical regions along a circular arc works particularly well with the single-sided analyzer and the Hall sensor analyzer of the present invention.

The present invention further provides a method for using the superparamagnetic particle imaging analyzer comprising providing a sample containing an analyte labeled with superparamagnetic nanoparticles, placing the sample in the field free region of the analyzer and exciting the superparamagnetic nanoparticles in the field free region to obtain a signal from paramagnetic response of the superparamagnetic nanoparticles, sensing and transmitting the signal, and analyzing the signal to obtain a characteristic of the analyte.

BRIEF DESCRIPTION OF THE DRAWINGS

FIG. 9C shows structure of an embodiment of a non-linear hybrid point of care chip of the present invention.

FIG. 10A shows structure of a first embodiment of the superparamagnetic particle imaging analyzer of the present invention where the analyzer is a co-linear analyzer; and FIG. 10B is an enlarged view of the center square in dotted line in FIG. 10A, showing structure of the hybrid point of care chip of the present invention as a disposable member at the location to fit into the analyzer.

FIG. 11A is a front view showing structure of a second embodiment of the superparamagnetic particle imaging analyzer of the present invention where the analyzer is an open-sided analyzer; and FIG. 11B is a side view showing structure of the same analyzer.

FIG. 12A shows structure of an "E" core excitation field for a third embodiment of the superparamagnetic particle imaging analyzer of the present invention; and FIG. 12B is a partial enlarged view showing the hybrid point of care chip of the present invention as a disposable member of the analyzer that fits into the analyzer.

FIG. 13A is a top view showing structure of a fourth embodiment of the superparamagnetic particle imaging analyzer of the present invention where the analyzer is a single sided analyzer with two concentrically placed transmit coils and separate receive coils; and FIG. 13B is a partial enlarged view showing structure of the hybrid point of care chip of the present invention as a disposable member of the analyzer and used in relation to the transmit coils and receive coils of the analyzer.

FIG. 15C is a side view showing structure of the analyzer of the present invention; and FIG. 15D is a top view showing structure of the analyzer of the present invention.

FIG. 19 shows the experimental results of SPNP concentration (ng/ml) as the horizontal axis in relation to magnetic response (Mox) as the vertical axis for the first, second, and third analytical regions in Example 1.

Figure 1:
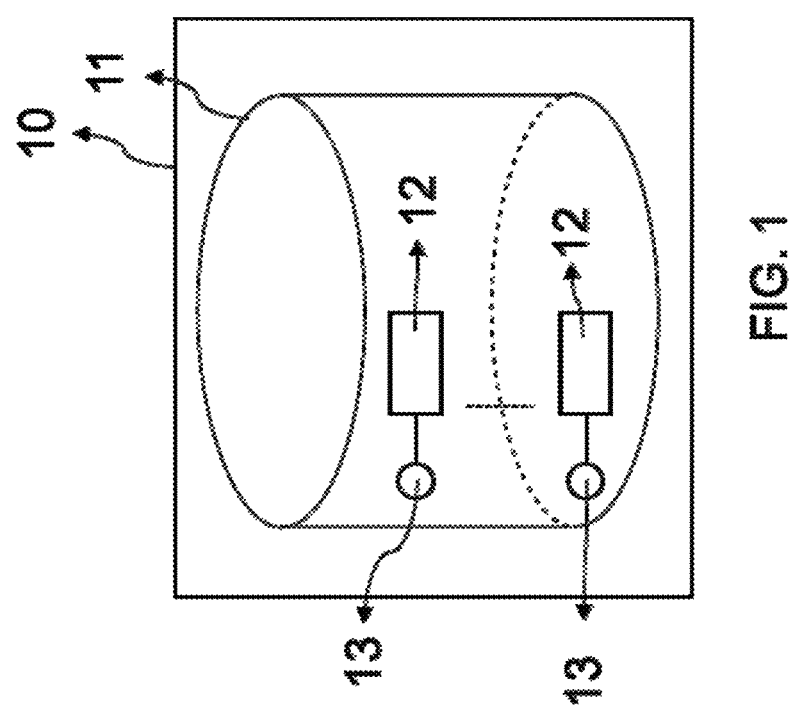
FIG. 1 shows a first embodiment of the analytical method of the present invention where one analytical region having one compartment is used, and one analyte is immobilized in the compartment.

Reference numbers are used in the figures as follows:
- 10—analytical region on the assay format (10' or 10a' denote different analytical region in a serial arrangement; 11—compartment (11', 11a, 11a', 11z denote different compartments in a serial arrangement(s)); 12—analyte; 13—superparamagnetic nanoparticle used to label the analyte 12, also called superparamagnetic particle, superparamagnetic nanoparticle label, or superparamagnetic particle label in the present invention;
- 20—hybrid point of care chip or chip array (20a, 20b, 20c, 20d, 20e, 20f, 20g, and 20h denote individual chips in the chip array); 210—analytical region in the chip 20 (210a, 210b, 210c, 210d, and 210e denote the first, second, third, fourth, and fifth analytical regions in a serial arrangement); 21—sample port; 22—reagent; 23—microchannel (23a, 23b, 23c, 23d, 23e denote different microchannels connecting different parts of the chip); 24—switching column; 25—packing material inside switching column 24; 26—absorption chamber; 27—absorption pads; 28—air vent;
- 30—SPI analyzer; 31—housing; 310—cylinder; 311—frame; 32—permanent magnet; 33—interior cylinder volume; 33a—inside cylinder of permanent magnet; 34—fastener; 35—excitation coil; 36—receive coils; 37—field free point (FFP) or field free region (FFR);

37'—linear field free point or region (FFL); 37b—null free non magnetizing region; 38—field of view (FOV); 39—arrows indicating selection field;

40—signal chain; 41—shield; 42—AC drive field; 43—DC drive field; 44—signal preamplification unit; 45—low pass filter; 46—analog to digital conversion; 47—signal amplifier; 48—barcode reader; 49—central processing unit (CPU); 50—blue tooth; 51—Wireless signal output (WIFI); 52—display; 53—(wireless) printer; 54—graphical user interface (GUI); 55—mobile application; 56—external 12-240V wall transformer;

60—Hall magnetic sensor; 60'—Hall element; 61—hollow shaft; 62—bias leads and signal out; 63—generated field line representations (phantoms of homogeneous magnetic quanta); 64—supporting base; 65—thermistor; 66—filter (for offset/cancel); 67—Hall signal pre-amplifier stage.

DETAIL DESCRIPTION OF THE PRESENT INVENTION AND EMBODIMENTS

In the present invention, the term "format" or "assay format" refers to the collection of parts, devices, and reagents necessary for carrying out an analytical method and to be used in that analytical method.

The analytical method of the present invention uses the superparamagnetic particle imaging technology which is based on the Langevin theory and detects and analyzes non-linear response of superparamagnetic nanoparticles (SPNP), primarily the harmonics thereof, to changing external magnetic field. Concentration of the superparamagnetic nanoparticle-labeled analytes immobilized on stationary phase is measured, in contrast to measuring free magnetic particles in a solution in the magnetic particle imaging technology. As a result, the method of the present invention only needs to measure total concentration of the analytes in the analytical region, not distribution of the tracers; as the analytical region is known, no reconstruction is needed to measure the concentration.

The method of the present invention uses superparamagnetic particle imaging technology that uses the spatial encoded non-linear response of superparamagnetic nanoparticles to the changing external magnetic field to quantify multiple analytes in the analytical regions of an assay chip simultaneously.

In the present invention, superparamagnetic particle imaging technology is used in in-vitro diagnostics. The selection of the materials used to make superparamagnetic nanoparticles is much broader than those used in in-vivo diagnostics, which may be Co, Fe, CoFe, Co alloys, ferrites, cobalt nitride, cobalt oxide, Co—Pd, Co—Pt, iron, iron alloys, Fe—Au, Fe—Cr, Fe—N, FeO, Fe—Pd, Fe—Pt, Fe—Zr—Nb—B, Mn—N, Nd—Fe—B, Nd—Fe—B—Nb—Cu, Ni, or Ni alloys.

In the present invention, the particles with different shape are used to give different harmonics. The superparamagnetic nanoparticles can be made in different geometric shapes, including but not limited spherical, elliptical, and tabular. Some particles are coated with different coating to generate different harmonics for analysis.

In the present invention, as particles with different sizes give different harmonics, the superparamagnetic nanoparticles are made in the size between 1 to 1000 nm.

In the present invention, the immobilized particles and free particles give different harmonics. It provides a method of separating the signal from immobilized superparamagnetic nanoparticles. As a result, the analytes can be directly measured after assay is run without having to wash the analytical regions to remove the unbound superparamagnetic nanoparticles.

In the present invention, the analytes can be anything that can be labeled with superparamagnetic nanoparticles and immobilized on the stationary phase, which include but not limited to organic molecules, biological molecules, peptides, polymers, amino acids, proteins, enzyme, antibodies, DNAs, RNAs, viruses, germs, cells, inorganic molecules and drugs.

In the present invention, the sample that can be measured includes but not limited to any body fluids, such as whole blood, serum, plasma, urine, saliva, feces, tears, sweat. It can also be extracts of liquids, solids, and gases.

The analytical method of the present invention is further illustrated in the following embodiments in connection with the figures. In the first embodiment of the analytical method of the present invention as shown in FIG. 1, the assay format where the analysis is conducted contains one analytical region 10, which consists of one compartment 11 that immobilizes analyte 12 labeled with superparamagnetic nanoparticle 13.

When the assay format is placed in a superparamagnetic particle imaging analyzer device of the present invention, a changing excitation field is applied to analytical region 10, and superparamagnetic nanoparticle 13 in analytical region 10 and compartment 11 respond and the harmonic signals are generated in the receive coils of the analyzer. Generated harmonic signal is directly proportional to the concentration of the superparamagnetic nanoparticles in compartment 11:

$$C = \frac{\hat{u}}{\hat{s}}$$

$\hat{u}$ is the signal received from compartment 11, $\hat{s}$ is the system function of compartment 11, and C is the concentration of the superparamagnetic nanoparticles, or concentration of the analyte in compartment 11. The system function can be obtained by measuring the response ($\hat{u}^o$) of a sample with known concentration ($C^o$):

$$\hat{s} = \frac{\hat{u}^o}{C^o}$$

Once the system function is obtained, by measuring the signals in the receive coil, the concentration of the analyte in the format can be determined.

Figure 2:
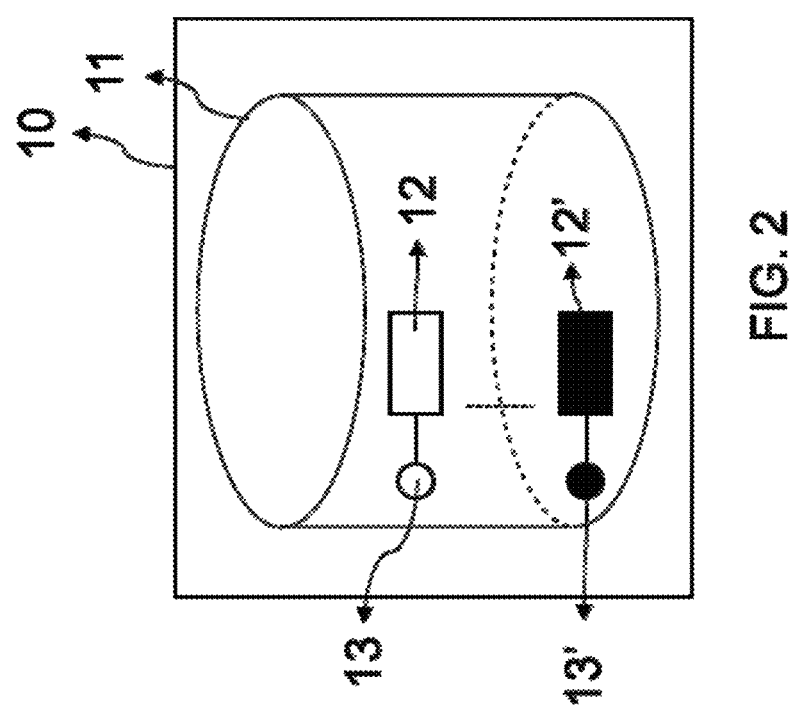
FIG. 2 shows a second embodiment of the analytical method of the present invention where one analytical region having one compartment is used, and multiple analytes are immobilized in the compartment.

In the second embodiment of the analytical method of the present invention as shown in FIG. 2, non-linear response of superparamagnetic nanoparticles to the changing external magnetic field to quantify multiple analytes on an assay format is used. The assay format contains one analytical region 10, which consists of one compartment 11. A total number of Z analytes (showing the first analyte as 12 and Zth analyte as 12') are immobilized in compartment 11. The number Z can be an integer of 1 to 20. Each of the analytes are labeled with a superparamagnetic nanoparticle (showing superparamagnetic nanoparticle 13 and 13' for labeling analytes 12 and 12', respectively).

When the assay format is placed in a superparamagnetic particle imaging analyzer of the present invention, a changing excitation field is applied to analytical region 10 and compartment 11, and all the superparamagnetic nanoparticles in compartment 11 respond and harmonic signals are generated in the receive coils of the analyzer. Concentration of the magnetic particles is directly proportional to its harmonics. The measured amplitude of the $n^{th}$ harmonics $A^n$ in compartment 11 is the summation of amplitude of the $n^{th}$ harmonics of all particles $A_i^n$ in compartment 11 (See Rauwerdink, A., "Simultaneous quantification of multiple magnetic nanoparticles," Nanotechnology, 21(45), 455101 (2010)):

$$A^n = \sum_{i=1}^{Z} A_i^n$$

The amplitude of the $n^{th}$ harmonics of particle i ($A_i^n$) is directly proportional to the concentration of particle i ($C_i$):

$$A_i^n = \circ A_i^n C_i$$

$\circ A_i^n$ is a constant that can be obtained by measuring the $n^{th}$ harmonics of a solution of particle i with known concentration ($C_i^\circ$):

$$\circ A_i^n = \frac{A_i^n}{C_i^\circ}$$

Since the ratio of all the harmonics of particles are concentration independent (See Rauwerdink, A., 2010), the concentrations for each particle in compartment 11 can be solved with the following equation:

$$Ax = b$$

where $$A = \begin{bmatrix} \circ A_1^3 & \cdots & \circ A_1^{2Z+1} \\ \vdots & \ddots & \vdots \\ \circ A_Z^3 & \cdots & \circ A_Z^{2Z+1} \end{bmatrix}$$

$$x = \begin{bmatrix} C_1 \\ \vdots \\ C_Z \end{bmatrix}$$

$$b = \begin{bmatrix} A^3 \\ \vdots \\ A^{2Z+1} \end{bmatrix}$$

In the equation, the harmonics are used from lower order to higher order, because the amplitude of the harmonics decrease rapidly as their orders get higher even though any harmonics can be used for the calculation. By measuring the $3^{rd}$ to $(2Z+1)$th harmonics in compartment 11, the concentrations of all the Z number of analytes are determined using the equation. A maximum of 1 (analytical region)•1 (compartments) •Z (SPNPs) analytes, in this case, 1 (analytical region)•1 (compartments)×20 (SPNP)=20 analytes can be analyzed simultaneously.

Figure 3:
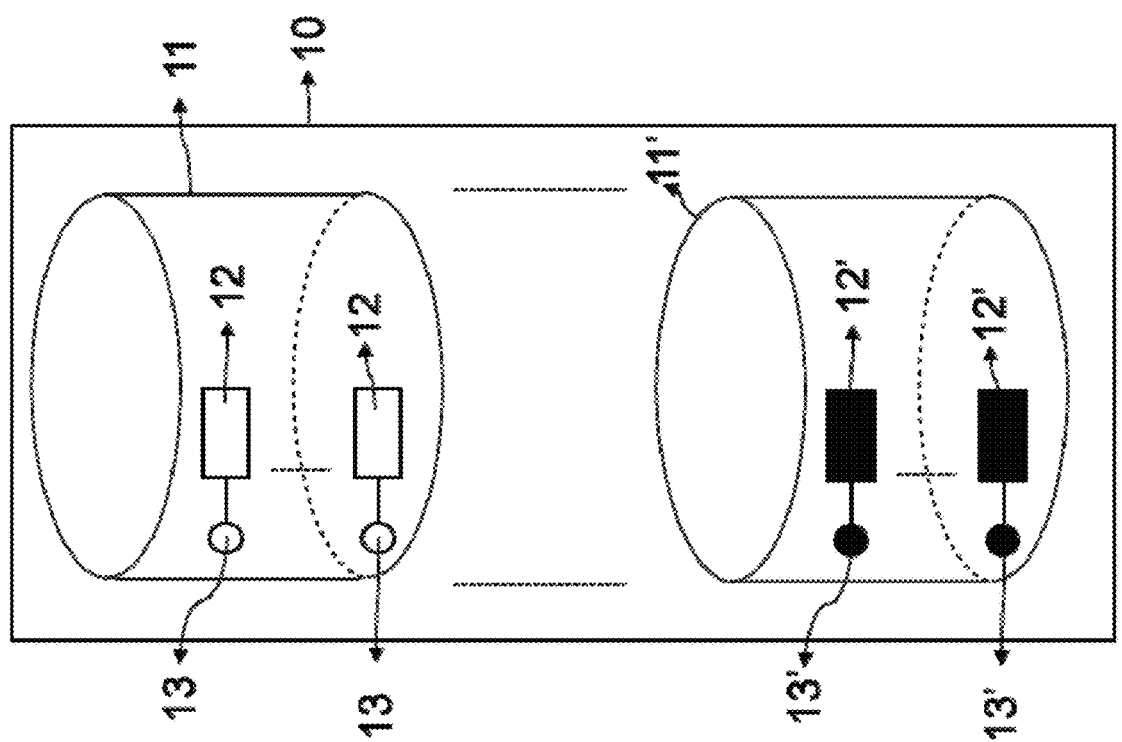
FIG. 3 shows a third and a fourth embodiments of the analytical method of the present invention where one analytical region having multiple compartments is used, and each compartment immobilizes a different analyte.

In the third embodiment of the analytical method of the present invention as shown in FIG. 3, non-linear response of superparamagnetic nanoparticles in spatial encoded compartments to the changing external magnetic field is used to quantify multiple analytes on the assay format. The assay format contains one analytical region 10, which consists of Y compartments (showing the first compartment 11 and the Yth compartment 11'). Y is an integer in the range of 1 to 20. Each compartment immobilizes a different analyte (showing the first analyte 12 in compartment 11 and the Yth analyte 12' in compartment 11'). Each analyte is labeled with a superparamagnetic nanoparticle (showing particle label 13 for analyte 12 in compartment 11 and particle label 13' for analyte 12' in compartment 11').

When the assay format is placed in a superparamagnetic particle imaging analyzer of the present invention, the focus field coils create a field free space (FFS) the size of one compartment 11. Since the structure of the analytical region 10, including the number of compartments, their shape, and location is known, the FFS can be moved based on the location of the compartments and applied to one compartment at a time. When the FFS is applied to compartment 11, a changing excitation field generated by the drive-field coils is applied to the compartment. Superparamagnetic nanoparticles 13 in the field-free compartment 11 respond and the harmonic signals are generated in the receive coils of the analyzer. Analyte 12 immobilized in compartment 11 is analyzed the way that is described in the first embodiment. After compartment 11 is analyzed, the FFS is moved to the next compartment and analyze the analyte immobilized in the next compartment. Repeat the same process until all the Y number of compartments in the analytical region 10 are analyzed. Thus, the Y number of analytes (showing only the first as 12 and Yth as 12') are all quantified. A maximum of 1 (analytical region) •Y (compartments)•1 (SPNPs) analytes, in this case, 1 (analytical region)•20 (compartments)•1 (SPNP)=20 analytes can be analyzed simultaneously.

In the fourth embodiment of the analytical method of the present invention, spatial encoded non-linear response of SPNP to the changing external magnetic field is used to quantify multiple analytes simultaneously on an assay format. The assay format is the same as the third embodiment as shown in FIG. 3, while a different analytical method is used in the configuration.

When the assay format is placed in a superparamagnetic particle imaging analyzer of the present invention, the focus field coils generate a Field Free Point (FFP). Since the structure of the analytical region 10, including the number of compartments (11, 11' . . . ), their shape, and their location is known, the FFP moves in a pre-determined route within analytical region 10. When a changing excitation field is applied to an FFP, it induces the magnetization of the SPNP 13, 13', . . . inside the FFP. Since the FFPs are spatial and temporal coded, the signals generated from FFP are also spatial and temporal coded. The induced magnetization length is directly proportional to the concentration of the magnetic particles 13, 13' . . . . The relationship between concentration of magnetic particles ($C_k(r')$) and the signals ($\hat{u}_k^{r'}$) at that location (r') and the time point can be expressed as: $\hat{u}_k^{r'} = \hat{s}_k \S \, k(r')C_k(r')$, $\hat{s}_k(r')$ is the system function. It can be determined by placing magnetic particle solutions with known concentration and measure the harmonic response at the same locations. With a known system function, the concentrations of magnetic particles $C_k$ (r') at each FFP can be determined as follows (Rahmer, J., et al, "3D Real-time Magnetic Particle Imaging: Encoding and Reconstruction Aspects," Proceedings of the First International Workshop on Magnetic Particle Imaging, 2014, p. 126-131):

$$C_k^Y(r') = \frac{\hat{u}_k^{r'}}{\hat{s}_k(r')}$$

$C_k^Y$ (r') is the concentration of magnetic particles at the sampling location (r') in the Yth compartment 11'. When the scanning is complete, the signals are processed based on where they are generated. The signals from the same compartment are processed together. In an ideal situation, the total concentration of magnetic particles in the Yth compartment 11' is proportional to the summation of the concentration of each location in the compartment:

$$C^Y = C_0^Y(\Sigma C_k^Y(r'))$$

$C^Y$ is the total concentration of the magnetic particles in the Yth compartment 11'. $C_0^Y$ is a constant which can be obtained by measuring the standard solution. In a non-ideal situation, a calibration curve between the summation of the signals and the total concentration can be established. By analyzing the first compartment 11 through the Yth compartment 11', the first analyte 12 to the Yth analyte 12' are quantified. A maximum of 1 (analytical region) •Y (compartments) •1 (SPNPs) analytes, in this case, 1 (analytical region) •20 (compartments) •1 (SPNP)=20 analytes can be analyzed simultaneously.

Figure 4:
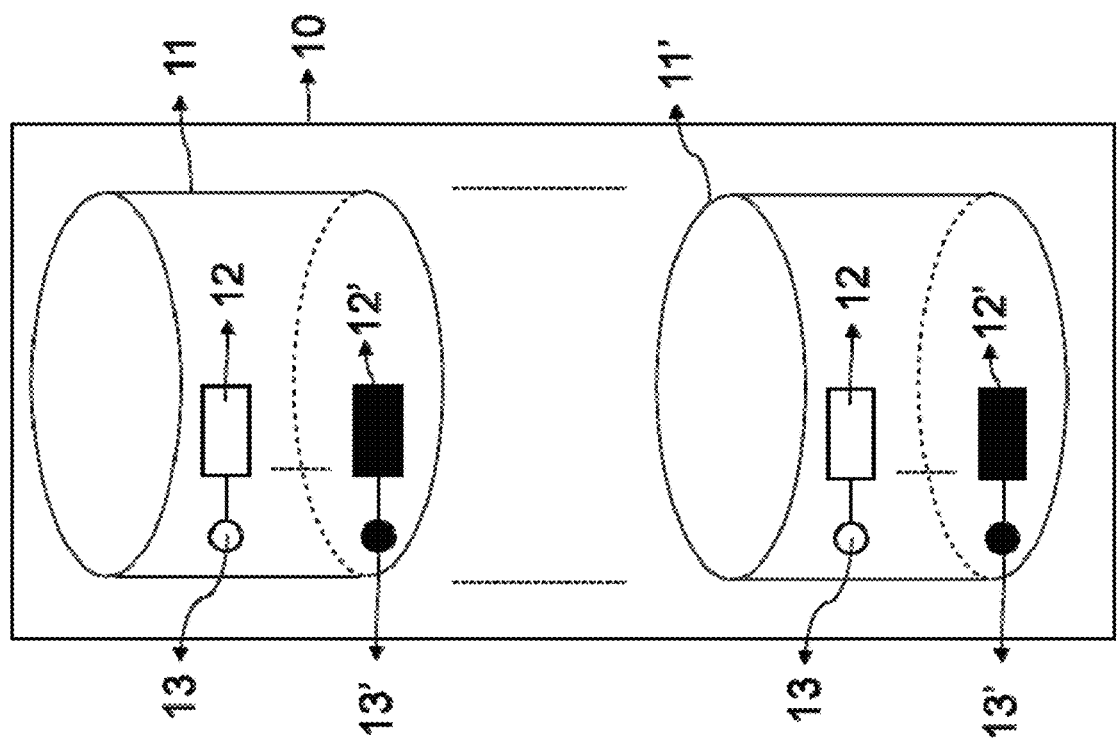
FIG. 4 shows a fifth and a sixth embodiments of the analytical method of the present invention where one analytical region having multiple compartments is used, and each compartment immobilizes multiple analytes.

In the fifth embodiment of the analytical method of the present invention as shown in FIG. 4, non-linear response of superparamagnetic nanoparticles in spatial encoded compartments to the changing external magnetic field is used to quantify multiple analytes on an assay format. The assay format contains one analytical region 10 which consists of Y number of compartments (showing the first compartment 11 and the Yth compartment 11'). Y is an integer in the range of 1 to 20. Each compartment immobilizes Z number of analytes (showing the first analyte 12 and the Zth analyte 12'). Z is an integer in the range of 2 to 20. The Z number of analytes are labeled with Z number of superparamagnetic nanoparticles, respectively (showing the first SPNP label 13 and the Zth SPNP label 13').

When the assay format is placed in a superparamagnetic particle imaging analyzer of the present invention, the focus field coils create a Field Free Space (FFS) the size of one compartment. Since the structure of analytical region 10, including the Y numbers of compartments 11, 11', . . . , their shape, and their location is known, the FFS can be moved based on the location of the compartments and applied to one compartment at a time. When the FFS applied to the first compartment 11, a changing excitation field generated by the drive-field coils is applied to the compartment. The SPNP in the field free compartment 11 respond and the harmonic signals are generated in the receive coils.

Analytes immobilized in compartment 11 are analyzed the way that is described in the second embodiment. Analytes 12, 12', . . . (a total Z numbers of analytes) in the first compartment 11 are quantified. After the first compartment 11 is analyzed, the FFS is moved to the second compartment and analyze that compartment, and so on, until the Yth compartment 11' in analytical region 10 is analyzed. Each compartment is analyzed the same way as compartment 11. A maximum of 1 (analytical region) •Y (compartments)•Z (SPNPs) analytes, in this case, 1 (analytical region)•20 (compartments)•20 (SPNP)=400 analytes can be analyzed simultaneously.

In the sixth embodiment of the analytical method of the present invention, spatial encoded non-linear response of SPNP to the changing external magnetic field is used to quantify multiple analytes simultaneously on the assay format. The embodiment is another method of analyzing the assay format shown in FIG. 4.

When the assay format is placed in a superparamagnetic particle imaging analyzer of the present invention, the focus field coils generate a Field Free Point (FFP). Since the structure of analytical region 10, including the number of compartments, their shape, and their location is known, the FFP moves in a pre-determined route within the analytical region. When a changing excitation field is applied to an FFP, it induces the magnetization of the SPNP inside the FFP. Since the FFPs are spatial and temporal coded, the signals generated from FFP are also spatial and temporal coded. The signals from the same compartment are processed together. The measured amplitude of the $n^{th}$ harmonics $A^n$ in a compartment is the summation of amplitude of the $n^{th}$ harmonics of all particles $A_i^n$ in that compartment as follows (Rauwerdink, A., Simultaneous quantification of multiple magnetic nanoparticles, Nanotechnology, 21(45), 455101 (2010)):

$$A^n = \Sigma_{i=1}^{Z} A_i^n (n=3,5, \ldots 2Z+1)$$

Using the $n^{th}$ amplitudes measured in the experiment ($A^n$) and the method described in the second embodiment, the amplitudes for each particle i ($A_i^n$) are determined. The amplitude of the $n^{th}$ harmonics of particle i ($A_i^n$) of the compartment is directly proportional to the total concentration of particle i ($C_i^{FFP}$) generated at FFP:

$$A_i^n = {\circ}A_i^n(C_i^{FFP})$$

${\circ}A_i^n$ is a constant that can be obtained by measuring the $n^{th}$ harmonics of a solution of particle i with known concentration. With known $A_i^n$ and ${\circ}A_i^n$, the total concentration of particle i ($C_i^{FFP}$) generated at FFP can be obtained:

$$C_i^{FFP} = \frac{A_i^n}{{\circ}A_i^n}$$

In an ideal situation, the concentration of magnetic particles i, or the concentration of the analyte i($C_i$) the is proportional to the total concentration of particle i generated at FFP ($C_i^{FFP}$)

$$C_i = (C_i^{\circ}(C_i^{FFP})$$

$C_i^{\circ}$ is a constant for particle that can be determined experimentally by a standard with known concentration. In a non-ideal situation, a calibration curve between $C_i$ and $C_i^{FFP}$ can be established with a series of standards in the concentration range of interest. After the analytes in one compartment are determined, all analytes in other compartments can be determined in the same fashion. Thus far, the concentrations of up to 1 (analytical region)•Y (compartments)•Z (SPNPs), in this case, 1 (analytical region)•20 (compartments)•20 (SPNPs)=400 analytes are determined simultaneously.

Figure 5:
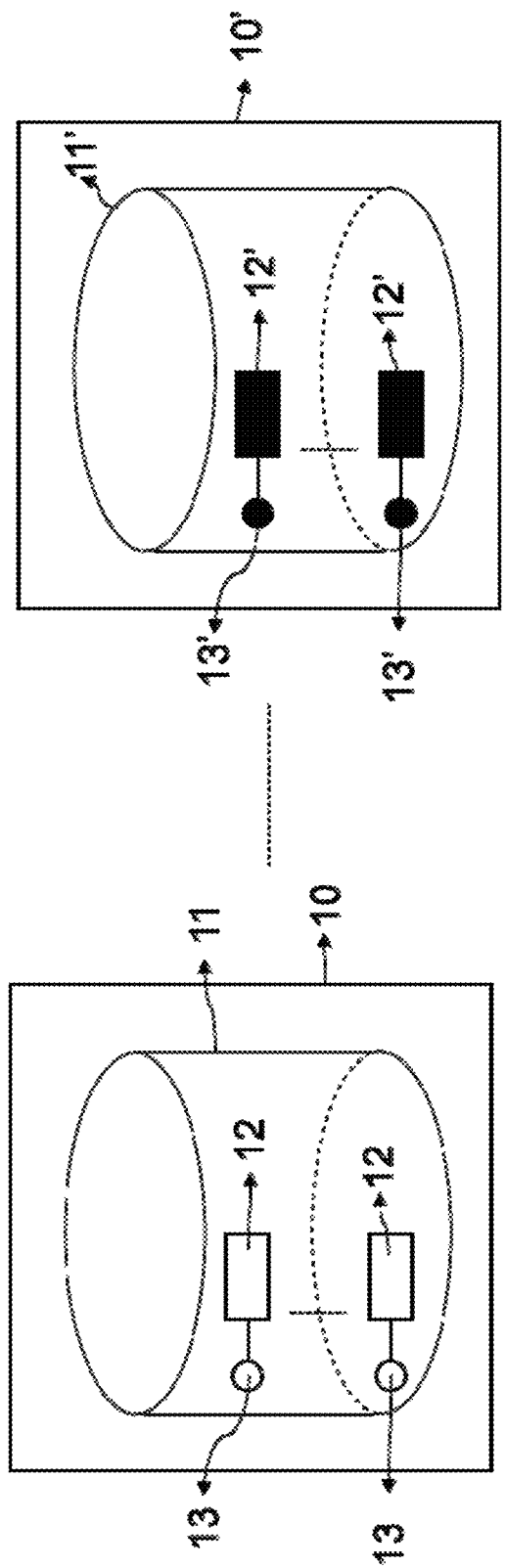
FIG. 5 shows a seventh embodiment of the analytical method of the present invention where multiple analytical regions, each having one compartment, is used, and each compartment immobilizes a different analyte.

In the seventh embodiment of the analytical method of the present invention as shown in FIG. 5, non-linear response of SPNP to the changing external magnetic field is used to quantify multiple analytes simultaneously on an assay format. The assay format contains X number of analytical regions (the first analytical region 10 and the Xth analytical region 10' are shown), and X is an integer in a range of 1 to 20. Each analytical region consists of one compartment (showing the first compartment 11 in the first analytical region 10, and the Xth compartment 11' in the Xth analytical region 10'). Each compartment immobilizes a different analyte (showing the first analyte 12 in compartment 11 and the Xth analyte 12' in the Xth compartment 11') labeled with an SPNP (showing the first SPNP 13 in the first compartment 11 and the Xth SPNP 13' in the Xth compartment 11'). The seventh embodiment of the analytical method is the same method as the first embodiment except that it's repeated X times. A maximum of X (analytical regions)•1 (compartments)•1 (SPNPs) analytes, in this case, 20 (analytical region)•1 (compartments)×1 (SPNP)=20 analytes can be analyzed simultaneously.

Figure 6:
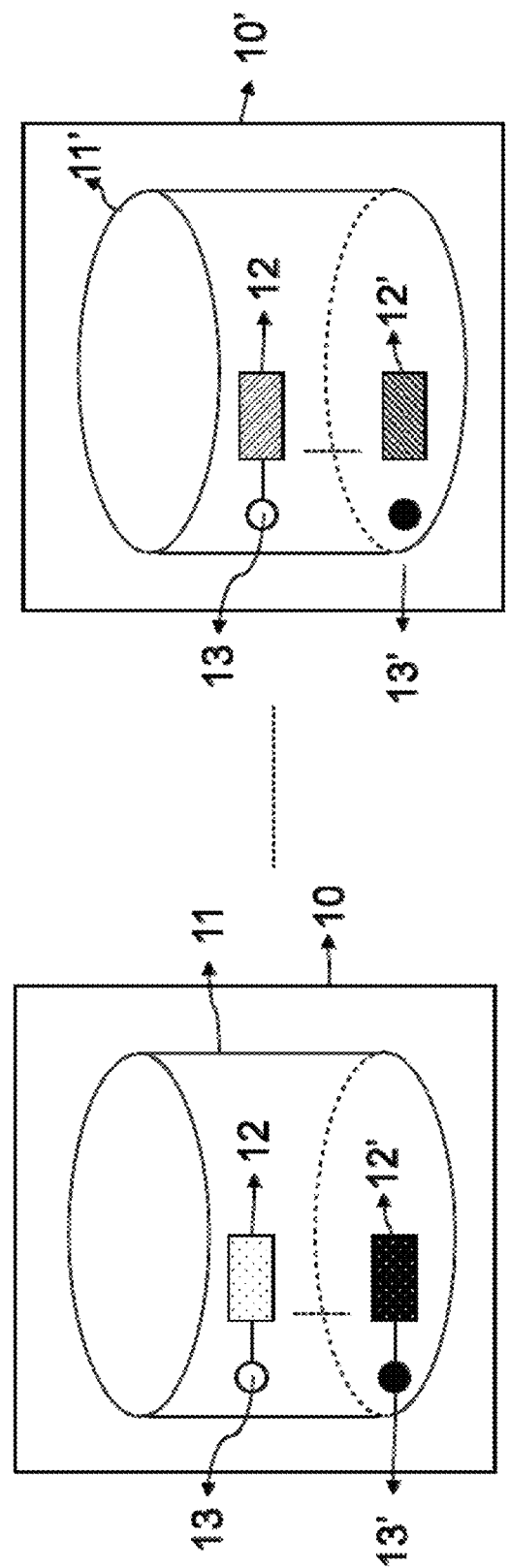
FIG. 6 shows an eighth embodiment of the analytical method of the present invention where multiple analytical regions, each having one compartment, is used, and each compartment immobilizes multiple analytes.

In the eighth embodiment of the analytical method of the present invention as shown in FIG. 6, non-linear response of SPNP to the changing external magnetic field is used to quantify multiple analytes simultaneously on an assay format. The assay format consists of X analytical regions (showing the first analytical region 10 and the Xth analytical region 10'), and X is an integer in a range of 1 to 20. Each analytical region consists of one compartment (showing compartment 11 in the first analytical region 10 and compartment 11' in the Xth analytical region 10'). Each compartment immobilizes Z number of analytes (showing both the first analyte 12 and the Zth analyte 12' in compartments 11 and 11'), and Z is an integer in a range of 1 to 20. Each analyte in one compartment is labeled with a different SPNP (showing the first label SPNP 13 for the first analyte and the Zth label SPNP 13' for the Zth analyte, respectively).

The analytical method used in the eighth embodiment is the same as the second embodiment, except that it's repeated X times. A maximum of X (analytical region)•1 (compartments)•1 (SPNPs) analytes, in this case, 20 (analytical region)•1 (compartments)×1 (SPNP)=20 analytes can be analyzed simultaneously.

Figure 7:
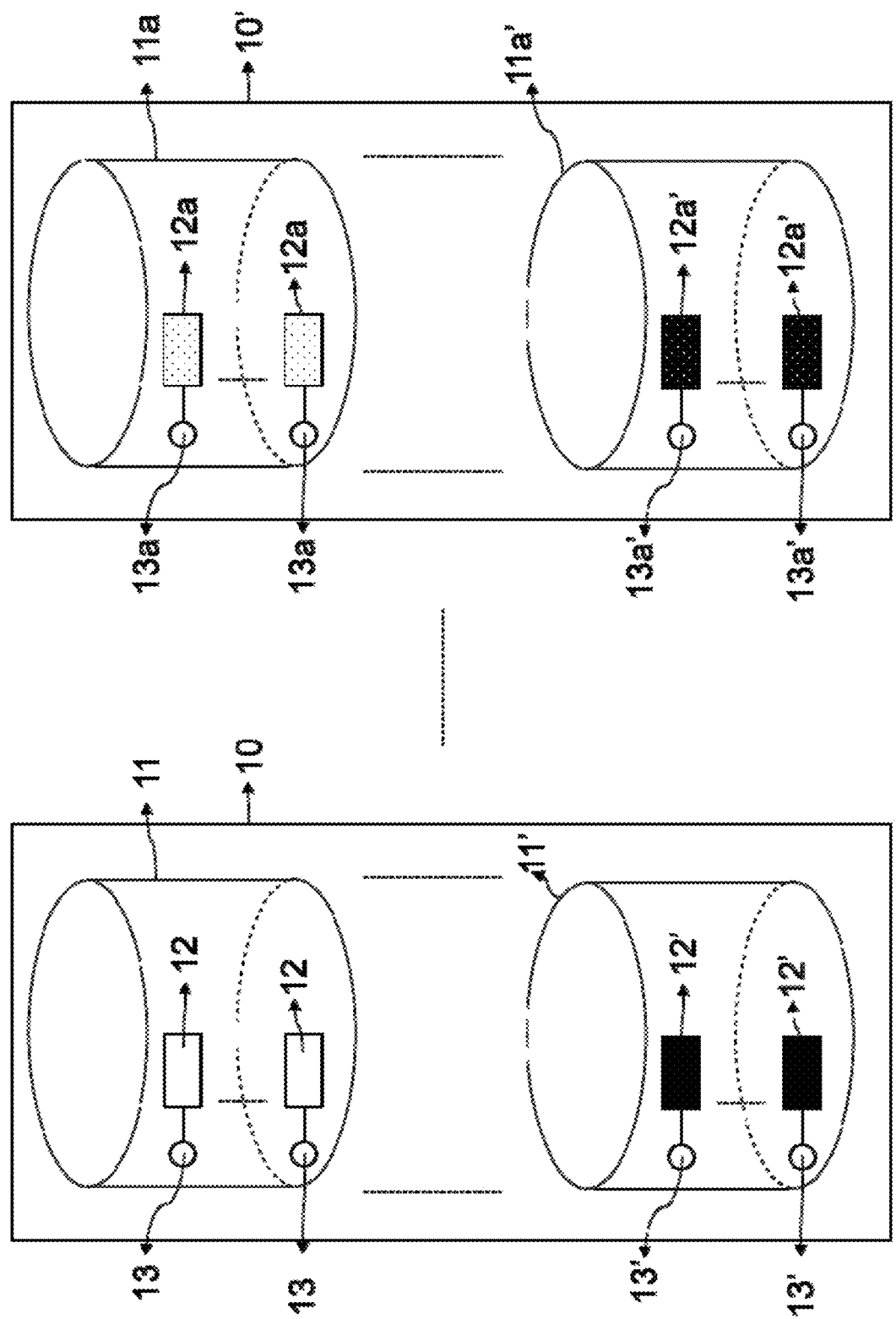
FIG. 7 shows a ninth and a tenth embodiments of the analytical method of the present invention where multiple analytical regions, each having multiple compartments, is used, and each compartment immobilizes a different analyte.

In the ninth embodiment of the analytical method of the present invention as shown in FIG. 7, non-linear response of SPNP in spatial encoded compartments to the changing external magnetic field is used to quantify multiple analytes on an assay format. The assay format contains X number of analytical regions (showing the first analytical region 10 and the Xth analytical region 10'), and X is an integer in a range of 1 to 20. Each analytical region consists of Y number of compartments (showing the first compartment 11 and Yth compartment 11' in the first analytical region 10 and the first compartment 11a and Yth compartment 11a' in the Xth analytical region 10'), and Y is an integer in a range of 1 to 20. Each compartment immobilizes a different analyte (showing the first analyte 12 in the first compartment 11 and the Yth analyte 12' in the Yth compartment 11' of analytical region 10, and the first analyte 12a in the first compartment 11a and the Yth analyte 12a' in the Yth compartment 11a' of analytical region 10') labeled with an SPNP (showing SPNP label 13 for analyte 12 in the first compartment 11 of analytical region 10, SPNP label 13' for analyte 12' in the Yth compartment 11' of analytical region 10, SPNP label 13a for analyte 12a in the first compartment 11a of the first analytical region 10', and SPNP label 13a' for analyte 12a' in the Yth compartment 11a' of the Xth analytical region 10').

The analytical method used in the ninth embodiment is the same as the third embodiment except that it's repeated X times. A maximum of X (analytical region) •Y (compartments)•1 (SPNPs) analytes, in this case, 20 (analytical regions)•20 (compartments)•1 (SPNP)=400 analytes can be analyzed simultaneously.

In the tenth embodiment of present invention, spatial encoded non-linear response of SPNP to the changing external magnetic field is used to quantify multiple analytes simultaneously on an assay format. The assay format is the same as the ninth embodiment as shown in FIG. 7, but the embodiment is a different method of analyzing the configuration.

The analytical method used in the tenth embodiment is the same as the fourth embodiment except that it's repeated X times. A maximum of X (analytical region) •Y (compartments)•1 (SPNPs) analytes, in this case, 20 (analytical regions)•20 (compartments)×1 (SPNP)=400 analytes can be analyzed simultaneously.

Figure 8:
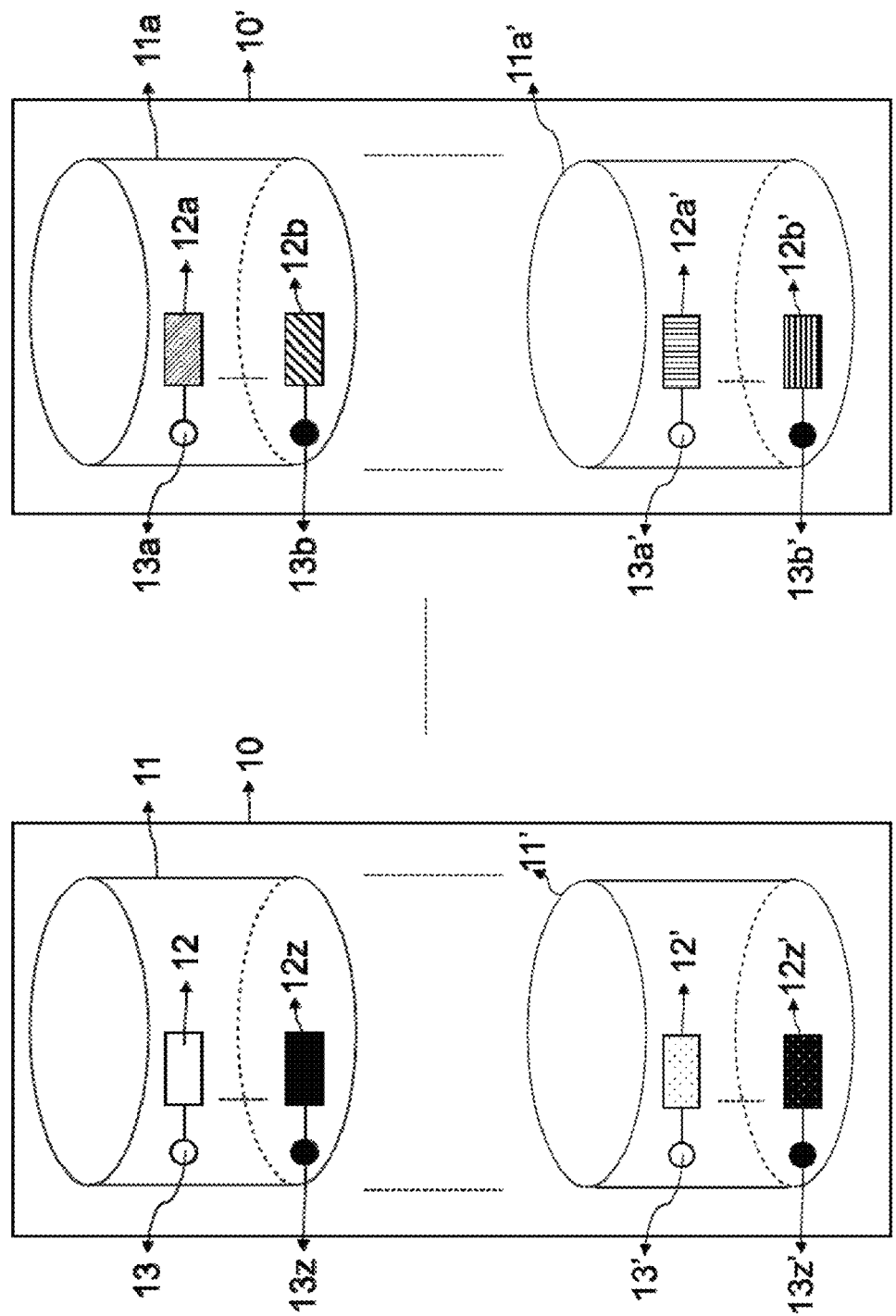
FIG. 8 shows an eleventh and twelfth embodiments of the analytical method of the present invention where multiple analytical regions, each having multiple compartments, is used, and each compartment immobilizes multiple analytes.

In the eleventh embodiment of the analytical method of the present invention as shown in FIG. 8, non-linear response of SPNP in spatial encoded compartments to the changing external magnetic field is used to quantify multiple analytes on an assay format. The assay format contains X number of analytical regions (showing the first analytical region 10 and the Xth analytical region 10'), and X is an integer in a range of 1 to 20. Each analytical region consists of Y number of compartments (showing the first compartment 11 and the Yth compartment 11' in the first analytical region 10 and the first compartment 11a and the Yth compartment 11a' in the Yth analytical region 10'), and Y is an integer in a range of 1 to 20. Each compartment can immobilize Z number of analytes (showing the first analyte 12 and Zth analyte 12z in compartment 11 and the first analyte 12' and Zth analyte 12z' in compartment 11' in the first analytical region 10; and the first analyte 12a and Zth analyte 12b in compartment 11a and the first analyte 12a' and Zth analyte 12b' in compartment 11a' in the Xth analytical region 10'), Z can be an integer in a range of 1 to 20. Each of the analytes are labeled with different SPNP, respectively (showing SPNPs 13 and 13z for analytes 12 and 12z, respectively, in compartment 11 and SPNPs 13' and 13z' for analytes 12' and 12z', respectively, in compartment 11' of analytical region 10; and SPNPs 13a and 13b for analytes 12a and 12b, respectively, in compartment 11a and SPNPs 13a' and 13b' for analytes 12a' and 12b', respectively, in compartment 11a' of analytical region 10').

The analytical method used in the eleventh embodiment is the same method as the third embodiment except that it's repeated X times. A maximum of X (analytical region)•Y (compartments)•Z (SPNPs) analytes, in this case, 20 (analytical regions)•20 (compartments) •20 (SPNP)=8,000 analytes can be analyzed simultaneously.

In the twelfth embodiment of the analytical method of the present invention, spatial encoded non-linear response of SPNP to the changing external magnetic field is used to quantify multiple analytes simultaneously on an assay format. The assay format is the same as the eleventh embodiment as shown in FIG. 8, but it is a different method of analyzing the configuration. The analytical method used in the embodiment is the same as in the sixth embodiment except that it's repeated X times. A maximum of X (analytical region)•Y (compartments) •X (SPNPs) analytes, in this case, 20 (analytical regions)•20 (compartments) •20 (SPNP)=8,000 analytes can be analyzed simultaneously.

As shown in the embodiments, the analytical methods of the present invention quantitatively measure analytes immobilized on stationary phase using superparamagnetic particle imaging technology. The analytical methods simultaneously measure the concentrations of multiple magnetically labeled analytes in an analytical sample immobilized on 3-dimensional stationary phase in a multiplexed assay by measuring the change in magnetic flux caused by magnetization of the magnetic labels.

In the present invention, the superparamagnetic particle imaging technology works well with the three-dimensional hybrid point of care chip of the present invention, and it can also be used in other assay formats, such as a lateral flow tests, microfluidic assays, "lab on a chip" devices, and stand-alone biosensors. There is an unmet need for high-throughput and cost-effective detection platforms for chemical and biological agents. These platforms can be utilized for a plethora of analytical and diagnostic applications including screening chemical libraries for drug development, toxicity studies, point-of-care diagnostics, and environmental monitoring. Conventional sensors generally use chemical, optical, spectroscopic, electrical impedance- or mass-based detection to interpret biochemical phenomena. Superparamagnetic particle imaging uses magnetic labels or magnetic nanoparticles of varying sizes, shapes, and compositions.

The analytical method of the present invention that uses the superparamagnetic particle imaging technology represents a new paradigm for performing direct and accurate detection of many medical diagnostic assays and companion drug monitoring tests. The superparamagnetic particle imaging technology not only extends the usefulness and sensitivity of magnetic based diagnostic assays, but also overcomes a major disadvantage of other magnetic based assays, that is, simultaneous detection of multiple analytes in a single measurement, an advantage optical based assays have enjoyed. The present invention makes it possible the development of many analytical assays requiring rapid, sensitive apparatus without the overwhelming associated costs of modern analytical laboratories. Tests such as DNA/RNA analysis, environmental testing, chemical and biological warfare detection, drugs of abuse screening, food supply quality sensing, can now be improved by utilizing the superparamagnetic particle imaging technology and producing a small, portable hand-held apparatus with biodegradable, disposable assay chips.

The present invention also provides a hybrid point of care chip that may be used in connection with the superparamagnetic nanoparticle based analytical method of the present invention.

The hybrid point of care chip of the present invention comprises a sample introduction region where the samples are introduced, switching columns where the samples flow are directed to different levels of the chip, analytical regions where the analytes are captured, enriched, and cleaned, a waste chamber where the excess of samples and washing fluids are collected, and the microchannels where different elements on the chip are communicated. In this design, the sample fluids can run from sample introduction region to absorption chamber automatically through capillary force. It may also include sample spitting channels, reagent storage reservoir, and mixing ports, and a pump.

The analytical regions of the hybrid point of care chip of the present invention house a 3-dimentional multi-compartment stationary phase where the analyte capturing materials are loaded. Sample fluids flow in three-dimensional paths to and through stationary phase of the analytical regions, which are themselves a 3-dimentional region. They are of known size and location, therefore the concentration of analytes can be measured without reconstruction.

The hybrid point of care format of the present invention is constructed of the stationary phase in the flow path of the liquid sample. The stationary phase is either directly dispensed in wells, grown by biological means, or consist of pre-forms of materials made of self-assembled plastics and polymers, silica or its equivalent, such as in organic/nonorganic structures. Examples are of stromatolites biologically made in nature, colloidal minerals such as agate or opal gels inorganically formed in hot springs, cellular wall and compartments in shoots of bamboo or stems and leaves of banana trees. All the natural structures are controlled by the DNA/RNA blueprints of biologic activity and can be used in the present invention.

The structures are placed into voids formed within a preferred laminate structure, though a bulk or cast structure can also be used for making the structures in the present invention. Referred to in the present invention as columns, capture regions, or analytical regions, they allow for the flow of the sample liquid to permeate through the functional "stationary phase" which in fact are porous materials with extremely large surface areas. The analytical regions are functionalized with similar chemistries of sandwich or competitive immunological assays or of DNA/RNA biochips well known in the art. Using antibodies or antigens as in immunoassays or small DNA probes labeled with magnetic nanoparticles, the analyte of interest is captured in these regions; or, as in a competitive assay, the analyte competes for a binding site on the functionalized stationary phase surface structure. The entire introduced sample flows through each of the vertical paths of either a rectilinear region or circular column from a 3-dimensional channel formed with a combination of hydrophilic/hydrophobic film laminations.

In a preferred form, the column voids are formed by a multi-lamination of films of which can be of paper, polymers, plastic, or metalized plastics or metals. These films can be purchased from Adhesive Research, 3M, DuPont Polymers, Pall, Coveme, and Tesa. The films have different surface coatings and properties, for example some being hydrophilic or hydrophobic. They can have thicknesses between 0.001" to 0.020", preferably 0.002" to 0.015" most preferably between 0.002" to 0.009." All of these laminations can be converted to the required form depending on the requirements of the magnetic reader system. The versions are of a multiplexed linear form, a more rapid circular column form and a partial disk with dispersed sample introduction means, capture or analytical regions, and ultimately a reservoir wick.

Each of the columns being in liquid communication of the other, flowing from bottom to the top of the column, and then flowing from the top to the bottom of the adjacent column and flowing from the bottom to the top of the next adjacent column, flowing eventually to the wick member (depending on the number of analytical regions). Each or all of the channels and columns may trap entrained air and form air pockets blocking flow of the fluid flow. If the trapped air becomes an issue, it's solved by placing a small vent at the top of each column. This vent allows trapped air to escape the fluidic channels and columns preventing a blocking of the liquid flow; but is small enough to not allow liquid to escape. These vents may have a porous plastic placed in the vent that close upon contact with a liquid or are made small enough that the surface tension of the liquid sample prevents the liquid from escaping, well known in the art. This size may range from 0.1 to 10 microns, and preferably, around 5 microns. Other means can prevent this occurring by insuring the capillary force is sufficient to move the entrained air ahead of the fluid flow, this is by selection of the materials or coatings in the channels.

Between the sample introduction region and the communicating channels that control the flow direction, speed, and 3-dimensional level of the desired analytical region is a smaller column that switches the flow of the liquid sample to the fluidic channel to the desired first analytical column. Referred to as a "switching column" in the present invention, it may or may not have a filter, blocking reagents, or conjugates (conjugates are a magnetic labeled recognition element, for example, in a sandwich assay, an antibody or protein that can be captured in an analytical column and measured). These on-board reagents eliminate the need of premixing the sample with a conjugate prior to application to the sample introduction region. Thus increasing shelf life and sensitivity and reducing the coefficient of variation of the assay.

The sample introduction means in the present invention may contain a mechanism for separation of erythrocytes. It prevents blocking of the columns because of the red blood cells ability to change their shape and/or their ability to release internal fluids that during hemolysis potentially can cause interference of the capture chemistry of the analytical region.

Each of the columns is in liquid communication with the other, either on the same plane or by purposely separating the analytical regions by dividing the sample flow to a distinct region to avoid chemical interference or to make the analysis of the resulting measurement more precise. An example is when an analyte in a sample is measured that is in relatively large concentration compared to an analyte from the same sample that is in small concentration. The resulting measurements tend to obscure the readings of the small concentration analyte. By changing the sample flow to a different 3-dimensional level one can minimize any interference from the 2 analytes.

The hybrid point of care chip of the present invention is a 3-dimensional multi-level construction with a stationary phase analytical region. It's constructed by laminating layers of films together. Some of the features of the hybrid point of care chips are incorporated into the films before lamination. Other features are created after lamination. The layers where the sample flows are called levels. Each chip can have 1-20 levels, preferably 1-10 levels The hybrid point of care chip consists of 1-5 sample introduction regions, 1-5 switching columns, 0-10 reagent reservoirs, 1-20 analytical regions, and 1-5 fluid absorption areas. The sample introduction regions, reagent reservoirs, analytical regions, and fluid absorption areas are connected by microfluidic channels and via (vertical interconnect access) allowing the samples to be divided and directed into different levels. The hybrid point of care chip can come with or without a liquid driving mechanism such as a diaphragm pump connected to the sample introduction region.

The films used in hybrid point of care chips are made out of plastic, adhesive, paper, wood, fiber, silicon, polydimethylsiloxane (PDMS), poly(methyl methacrylate) (PMMA), fiberglass, cellulose, polysaccharide, protein polymer, or calendared particles. The surface of the films can be modified to have necessary properties, including hydrophobicity and hydrophilicity. Each sample introduction region can be with or without erythrocyte cell separation mechanism. It can also contain reagents necessary for recognizing and immobilizing analytes of interest in the sample. The sample introduction region can accommodate 1-200 micro liter of samples.

The samples can be whole blood, plasma, serum, urine, saliva, tears, sweat, feces extracts, DNA/RNA extracts, solution containing antigen, antibodies, enzymes, proteins, peptides, amino acids, hormones, organic and inorganic molecules, biomarkers, industrial contaminants, pathogens, virus, cells, cell culture extracts, and environmental samples.

The reagent reservoirs contain reagents necessary for recognizing and immobilizing analytes of interest, including magnetic, fluorescent, chemiluminescent and radioactive particles; magnetic, fluorescent, chemiluminescent and radioactive particles functionalized with antibody, protein, DNA/RNA probe and chelating reagent; fluorescent, chemiluminescent and radioactive labeled antibody, protein, DNA/RNA probe and chelating reagent. The reservoirs can be in the same sample path or different sample paths. The reagents can be placed in the reservoirs directly or absorbed onto a solid support.

Each analytical region consists of 1-20 sections of stationary phase assembled together. Different sections of an analytical region can be made out of the same or different stationary phases. The stationary phase can be particles made out of plastic, silica, glass, alumina, organic polymer, inorganic polymer, and biodegradable polymers; or pores membranes constructed out of plastic, fiber, polymers, polysaccharides, celluloses, paper, wood, biological constructions, biological scaffolds, fiber glass, biodegradable polymers and protein polymers; water insoluble gel; colloids. The membranes can be woven, non-woven, or calendared particles. The stationary phases are functionalized by physical adsorption or covalent bonding with recognition reagents specific to the analytes of interest. The stationary phases can be preformed to the shapes and sizes of the analytical regions, and placed into the regions, or dispensed into the region directly. The analytical region can be constructed within one level, or across several levels.

Each absorption area consists of a chamber with fluid absorption pads. The pads are made out of pores membranes constructed out of plastic, fiber, polymers, polysaccharides, celluloses, paper, wood, biological constructions, biological scaffolds, fiber glass, biodegradable polymers and protein polymers; hydrogel; particles, calendared particles.

The materials of the laminations can be biodegradable and made with a variety of polymers, fibers, celluloids and papers that degrade rapidly so as not to be detrimental to the environment. An example is that there is not a conventional plastic cassette to support the test structure; the support is integrated in to the laminate test design and is self-supporting.

Figure 9A:
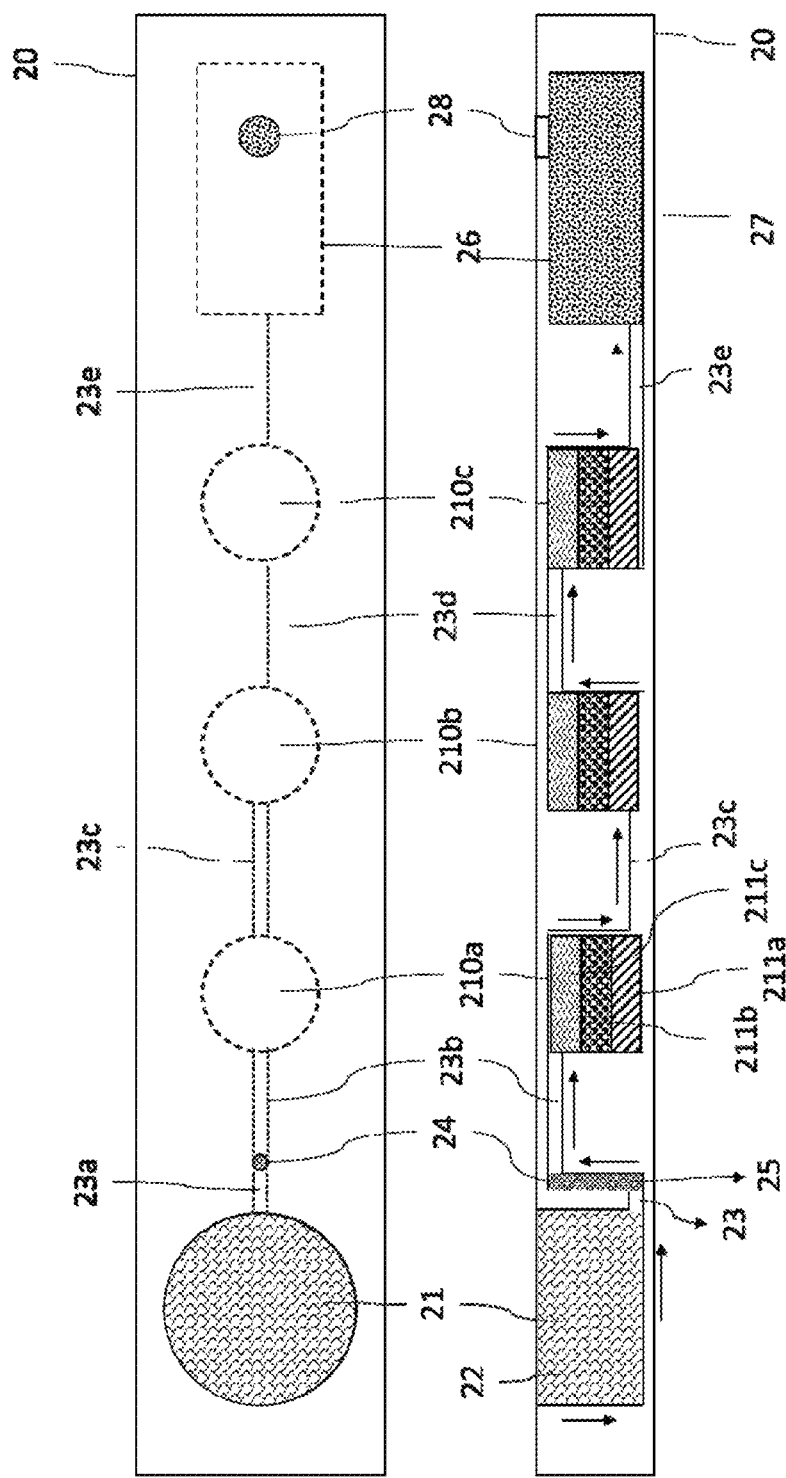
FIG. 9A shows corresponding top and side views of the structure of the hybrid point of care chip of the present invention, with the top view at the upper portion and side view at the lower portion.

In connection with FIGS. 9A through 9D, the structure of the hybrid point of care chip of the present invention is further explained in the following embodiment. In one embodiment of the hybrid point of care chip of the present invention as shown in FIG. 9A, the three-dimensional hybrid point of care chip 20 of the present invention comprises one sample introduction region in the form of a sample introduction region 21, three analytical regions 210a, 210b, and 210c, switching column 24, and fluid absorption area in the form of absorption chamber 26 with an air vent 28. Sequentially, sample introduction region 21 and switching column 24 are connected by microchannel 23a; switching column 24 and the first analytical region 210a are connected by microchannel 23b; the first analytical region 210a and the second analytical region 210b are connected by microchannel 23c; and the second analytical region 210b and the third analytical region 210c are connected by microchannel 23d. The first analytical region 210a is a multi-compartment analytical region having a first compartment 211a, a second compartment 211b, and a third compartment 211c. Arrows in FIG. 9A show flow of the sample in the chip.

Reagents 22 needed for the chemical and biological reactions of the assay occurred on the chip are preloaded inside sample introduction region 21. Analytical samples are in the amount of 1-500 microliters, normally 1-100 microliters, and preferably 5-10 microliters. Samples may be pretreated or not treated, including but not limited to serum, plasma, saliva, sweat, tear, sputum, urine; extracted surface wipes on swabs and even semi-solids such as cell culture and fecal matter, whole blood (if a red blood separation mechanism is incorporated in the in structure of sample introduction region 21 for the whole blood analysis).

Samples are added to sample introduction region 21 and quickly solubilizes in reagents 22. Samples mix with reagents 22, pass microchannel 23a, and enter switching column 24. The function of switching column 24 is to direct sample to different level. In the embodiment, switching column 24 leads sample to the upper level of analytical region 210a of the chip 20 via microchannel 23b (it can also switch the sample flow to the lower level if needed). In the multilevel design of the present invention, switching column 24 can switch the sample to any level as desired. Packing materials 25 in switching column 24 also serve as a filter to remove the solid impurities in the sample and deliver clean sample to the analytical region. After the sample passes switching column 24, it passes microchannel 23b and enters the first analytical region 210a.

Generally, the analytical regions in the hybrid point of care chip of the present invention can be made with 1-20 compartments, typically 1-10 compartments, and preferably 1-5 compartments. In the embodiment, there are 3 compartments, 211a, 211b, and 211c.

Each compartment can be made with the same or different stationary phase depending on the assay. The stationary phase can be particles made out of plastic, silica, glass, alumina, organic polymer, inorganic polymer, and biodegradable polymers; or pores membranes constructed out of plastic, fiber, polymers, polysaccharides, celluloses, paper, wood, biological constructions, biological scaffolds, fiber glass, biodegradable polymers and protein polymers; water insoluble gel; colloids. The membranes can be woven, non-woven, or calendared particles. The stationary phases are functionalized by physical adsorption or covalent bonding with recognition reagents specific to the analytes of interest. The stationary phases can be pre-formed to the shapes and sizes of the analytical regions, and placed into the regions, or dispensed into the region directly. The analytical region can be constructed within one level, or across several levels. Each compartment can immobilize different analytes.

When the sample passes the first analytical region 210a, the analytes of interest are captured. The rest of the sample leave the first analytical region 210a. In the process, the analytes are separated by the compartment with selective stationary phase. They are also enriched in the compartment and cleaned by the passing sample fluid. Because of the multi-compartment design in the present invention, it makes the multiplexing possible.

After passing microchannel 23c, the sample then enters the second analytical region 210b. Analytical region 210b can have the same construction, including the number of compartments, the materials of stationary phase, and number of different capturing materials loaded in the compartment, as the first analytical region 210a. After passing the second analytical region 210b, the second set of analytes are separated and captured. The sample continues to move past the microchannel 23d and enters the third analytical region 210c. The third set of analytes are separated in the third analytical region 210c. The remaining sample fluid and excess reagents are absorbed by fluid absorption pads 27 in absorption chamber 26. Absorption pads 27 are made out of pores membranes constructed out of plastic, fiber, polymers, polysaccharides, celluloses, paper, wood, biological constructions, biological scaffolds, fiber glass, biodegradable polymers and protein polymers; hydrogel; particles, or calendared particles.

In the present invention, the hybrid point of care chip can be made with 1-20 analytical regions, normally 1-10 analytical regions, and preferably 1-6 analytical regions.

Figure 9B:
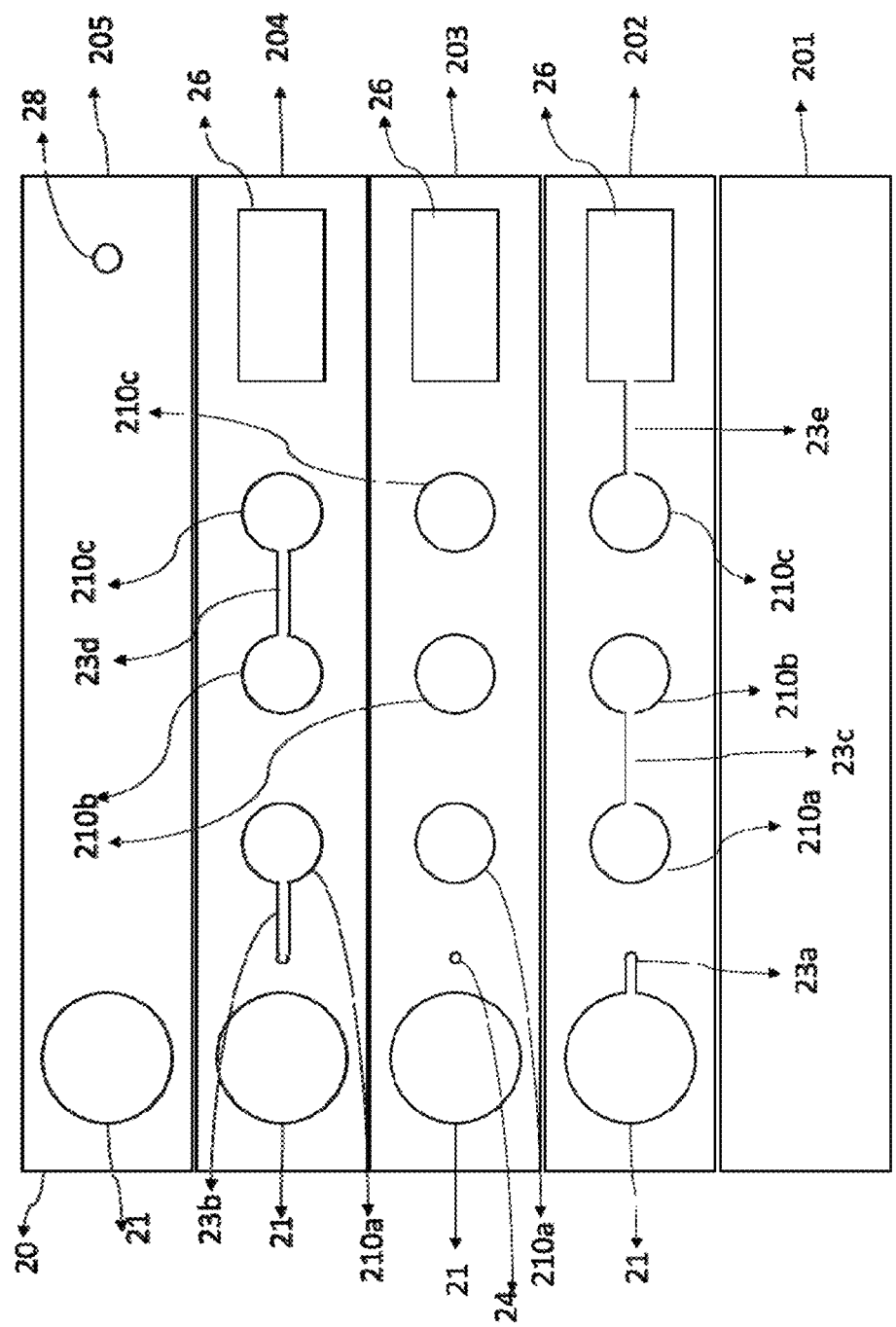
FIG. 9B is an exploded view showing structure of layers and parts that make up the hybrid point of care chip of the present invention.

The construction of the hybrid point of care chip of the present invention is shown in FIG. 9B. The hybrid point of care chip 20 of the present invention is a 3-dimentional multi-level construction with solid phase analytical regions 210a, 210b, and 210c. Chip 20 is constructed by laminating layers of films together, including bottom layer 201, in the embodiment.

In the present invention, some of the features of the hybrid point of care chips are incorporated into the films before lamination. Other features are created after lamination. The layers where the sample flows are called levels. Each chip can have 1-20 levels, preferably 1-10 levels.

In the present invention, the hybrid point of care chip consists of 1-5 sample introduction regions, 0-10 reagent reservoirs, 1-20 analytical regions, and 1-5 fluid absorption areas. The sample introduction regions, reagent reservoirs, analytical regions, and fluid absorption areas are connected by microfluidic channels and via (vertical interconnect access) allowing the samples to be divided and directed into different levels. The hybrid point of care chip can come with or without a liquid driving mechanism.

The films used in hybrid point of care chips are made out of plastic, adhesive, paper, wood, fiber, silicon, polydimethylsiloxane (PDMS), poly(methyl methacrylate) (PMMA), fiberglass, cellulose, polysaccharide, protein polymer, calendared particles. The surface of the films can be modified to have necessary properties, including hydrophobicity and hydrophilicity.

In construction of chip 20 as shown in FIG. 9B, chip 20 consists of 5 layers of films, that is, bottom layer 201, bottom channel layer 202, middle layer 203, top channel layer 204, and top layer 205. The thickness of the films is adjusted based on the requirement of the design. The microchannel is formed by the channel layers 202 and 204. When layers 201, 202, and 203 are assembled, microchannel 23a that links sample introduction region 21 to switching column 24, microchannel 23c that links the first analytical region 210a to the second analytical region 210b, and microchannel 23e that links the third analytical region 210c to absorption chamber 26 are formed. After adding layers 204 and 205, microchannel 23b that links switching column 24 to the first analytical region 210a, and microchannel 23d that links the second analytical region 210b to the third analytical region 210c. At the same time, switching column 24 and analytical regions are constructed. The structure allows the sample to travel horizontally between locations through microchannel and vertically between levels through switching columns and analytical regions. The stationary phase materials need to be placed into switching columns and analytical regions, by dispensing particles or placing preformed membranes, before layers 204 and 205 are added on to complete the construction of the chip.

Chip 20 shown in FIG. 9B is for illustration only. Additional features such as more analytical regions or reagent reservoirs can be added onto the chip. The number of levels can be increased by adding more layers of film.

FIG. 9C depicts another embodiment of the hybrid point of care chip of the present invention that takes advantage of the flexibility that, unlike lateral flow design, the hybrid point of care chip of the present invention uses microchannel to communicate between locations and therefore, the features on the chip do not have to be arranged in a linear fashion. The construction of the chip 20 in the embodiment is the same as those described in FIGS. 9A and 9B except that the analytical regions 210a, 210b, 210c, 210d, and 210e are arranged along a circular arc. The arrangement allows the chip 20 or the detector to move in a circular motion, which can significantly reduce the design and manufacturing cost.

Figure 9D:
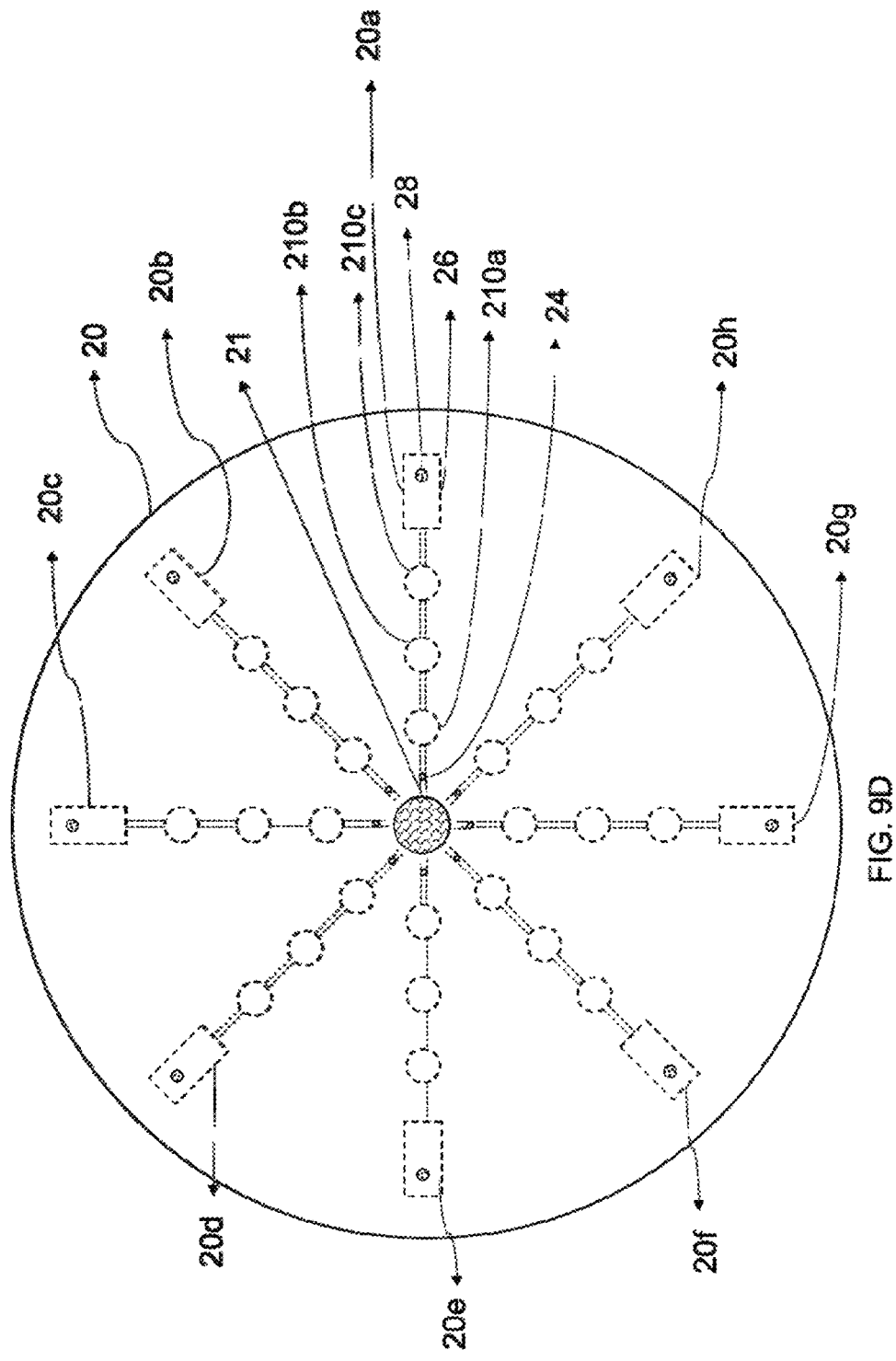
FIG. 9D shows structure of an embodiment of a hybrid point of care chip array of the present invention.

Another embodiment of the hybrid point of care chip of the present invention is in the form of a chip array as shown in FIG. 9D, where chip 20 is in the form of a chip array having 8 individual chips 20a, 20b, 20c, 20d, 20e, 20f, 20g, and 20h. Construction of these individual is the same as those described in FIGS. 9A and 9B except that each layer of films has multiple sets of chip features and all the chips on the same disk share one sample introduction region 21 in the centralized location as shown in FIG. 9D. In the embodiment, each individual chip has 3 sequentially ordered analytical regions 210a, 210b, and 210c. The arrangement allows to test multiple sets analytes from a single sample. Each individual chip is completely independent from other chips in the chip array 20. Therefore, no chemical and/or biological incompatible analysis can be conducted in a single run.

Depending on the construction, the hybrid point of care chip of the present invention can be used with different types of detection systems. Preferably, the detection methods for the hybrid point of care chip is a magnetic, acoustic, or radioactive based detection method, because these methods do not rely on the transparency of the analytical regions. They can measure the signals from entire 3-dimensional stationary phase body, not just surface.

The more preferred methods are magnetic based detections, including Superparamagnetic Particle Imaging (SPI), Magnetic Particle Imaging (MPI), Magnetic Particle Spectroscopy (MPS), Total Accumulation of Magnetic Particle, Magnetic Inductance, AC magnetic susceptometry, CMOS AC susceptometry, Hall Effect, Magnetoresistance, Giant magnetoresistance (GMR), Colossal magnetoresistance (CMR), Superconducting Quantum Interference Devices (SQUIDs), Magnetic Relaxometry, Magnetic Resonance Imaging (MRI) spin relaxation times. The more preferable magnetic detection methods are superparamagnetic particle imaging, Magnetic Particle Imaging (MPI), Magnetic Particle Spectroscopy (MPS), Total Accumulation of Magnetic Particle, Magnetic Inductance, Hall Effect.

The most preferable magnetic detection methods are superparamagnetic particle imaging, Magnetic Particle Spectroscopy (MPS), Total Accumulation of Magnetic Particle, Magnetic Inductance, Further, if the stationary phase inside the analytical regions is made out of light transmittable materials, including glass, quarts, transparent plastics, optical based detection methods can be used, including fluorescence, UV-Vis, laser, chemiluminescence.

The hybrid point of care chip of the present invention has advantages of the versatility and flexibility of the microfluidic device, the low cost and simplicity of lateral flow test, and low background and high sensitivity of Elisa assay; it is also capable of multiplexing. The hybrid point of care chip differs from other designs in its multileveled and multicompartments analytical regions filled with stationary phase. The multi-compartment construction allows several compartments each loaded with different capturing materials be stacked together and achieve additional dimension of multiplexing. The stationary phase in the analytical regions immobilizes the analytes labeled with appropriate reporter, such as magnetic particles, radioactive material, acoustic active materials. Because of its huge surface area, it enriches the analytes in the sample and significantly improves the sensitivity. Because of its heterogeneous nature, the interference materials are washed away, it has much lower background than other assay design.

The hybrid point of care chip of the present invention solves all the issues associated with the lateral flow format. By connecting the sample introduction region directly to the analytical region with a microfluidic channel, it eliminates all the cross sections existed in lateral flow format. Since the samples are delivered directly to analytical regions, it significantly reduces the variations caused by the inconsistent membrane between the sample introduction region and test lines in lateral flow format. Since the microfluidic channels are enclosed, it doesn't have the leakage issues the lateral flow strips have because of their open edges. In lateral flow format, the capturing materials are striped onto the membrane. Due to the variation of the membrane, the striping conditions, and striping equipment, the analytical regions are highly inconsistent. In the hybrid point of care format, the analytical regions are filled with 3-dimensional stationary phase made out of highly organized materials. The variation of among the stationary phases are less than 0.1%. While overcoming all the problems that lateral flow format, hybrid point of care format retains the advantage of the ease of use and low cost the lateral flow format has.

The hybrid point of care format of the present invention also provides the answers to these challenges in the microfluidic format. By placing permeable 3-dimensional stationary phases in the path of microchannel, it allows the analytes and analytes only to be captured and accumulated while letting everything else pass through. In the process, it enriches the analytes, which enhances the sensitivities significantly. At the same time, it removes everything that are not related to analytes, which reduces the noise significantly. Because of this design, there is no sample pretreatment needs and no sample purification process to be added to the devices. By taking advantage of microfluidics, the multi compartment stationary phase is designed. Each compartment can immobilize different analytes. By coupling hybrid point of care format with superparamagnetic particle imaging technology, concurrent detection of multiple analytes can be accomplished. The multi-level design of the hybrid point of care format allows analytes that are not chemically and/or biologically compatible be directed to different path and/or different level and analyzed simultaneously. Since the hybrid point of care format is made out of laminates, it suits for automated large scale and low cost production, comparable to lateral flow format.

Further, the chemical and biological process occurred on stationary phase of hybrid point of care format has 300-10,000 times larger surface area than a typical ELISA assay format depending on the material used, which greatly enhances the sensitivity without the trouble of reagent handling, operating, and long waiting.

The hybrid point of care of the present invention is a new and innovative format that accomplishes sensitive, quantitative, and rapid diagnostic assays using small volumes of biological, environmental or chemical fluids. It may employ solution, colloidal or suspension particles of all kinds, including magnetic particles, to label the analyte of interest or to compete with a binding site that measures the reduction of a label. It is of a 3-dementional heterogeneous design and function using stationary phases and laminates including those made from bio-degradable materials without the use of traditional medical plastic cassettes. Volumes of 10 micro liters or less are typical sample sizes for serum, plasma, saliva, sweat, tear, sputum, urine; extracted surface wipes on swabs and even semi-solids such as cell culture and fecal matter. Further, an integrated red blood cell separation technique and device may be used to separate and prevent minimal hemolysis, and the hybrid point of care format requires less than a drop of whole blood for an analysis with an assay time of shorter than 5 minutes.

The present invention produces rapid development of the quantitative analysis with run time in the single digit minutes as opposed to 20 plus minutes in the conventional lateral flow tests, along with any necessary normalization. The significant reduction in the run time is due to reduced sample volume and minimal surface kinetic and hydrodynamic interactions.

The hybrid point of care format and chip of the present invention allows the coefficient of variations for routine assay to be below 10% at limit of detection (LOD), typically pico-gram levels.

The present invention further provides a superparamagnetic particle imaging analyzer which is the instrument designed based on superparamagnetic particle imaging technology, is used to create a Field Free Point (FFP) and/or Field Free Line (FFL) to spatially and temporally encode the signals generated by the superparamagnetic nanoparticles, record the signals, and convert the signals to the concentrations of the analytes on the entire chip in one single measurement.

According to one aspect of the present invention, another superparamagnetic particle imaging analyzer is used to create a Field Free Space (FFS) that covers the individual compartments, record the total signals generated from each compartment, and convert the signals to the concentrations of the analytes on the entire chip in one single measurement.

According to one aspect of the present invention, another superparamagnetic particle imaging analyzer is used to analyze multiple analytes labeled with different SPNP concurrently.

In the first embodiment of the superparamagnetic particle imaging analyzer of the present invention as shown in FIG. 10A, the device is a co-linear superparamagnetic particle imaging analyzer. The analyzer 30 comprises a housing 31, a pair of permanent magnets 32 and 32', a pair of excitation coils 35 and 35', and a pair of receive coils 36 and 36'.

In the embodiment, housing 31 is in the form of cylinder 310, and inside the cylinder 310, each of the permanent magnets is cylindrical with interior cylinder volume 33. The permanent magnets 32 and 32' are made of rare Earth alloy, such as NdFeB, and mechanically forced and held with their matching magnetic poles towards one another (that is, North pole of the first magnet facing North pole of the second magnet, or South pole of the first magnet facing South pole of the second magnet) with a fixture and fasteners 34, during which process a field free point (FFP) or field free region (FFR) 37 is formed where there resides a neutral field. Theoretically, it is a single point, but in fact, it is a region that is formed by the impinging fields lines by the competing magnetic force fields. (See Gleich, B., 2005, Knopp, T., 2012) The structure and arrangement form a stable homogeneous direct current (DC) field fee region (FFR), which can also be accomplished by a pair of Helmholtz coils driven by a DC amplifier. Permanent magnet pair 32 and 32' allows less complex and expensive platform to be assembled but lacking any adjustability.

As shown in FIG. 1B, the hybrid point of care chip of the present invention comprises the functioning mechanisms of sample handling, collection (as sample introduction region 21), dispersion, capture (as analytical region, also called region of interest (ROI), 210), and waste collection (as fluid absorption area 26) in a single multiplexed device 20, and is the disposable member of the superparamagnetic particle imaging analyzer 30 of the present invention.

Forming an alternating current (AC) inside the field free region 37 is accomplished by providing an AC driven field forming Helmholtz pair of excitation coils 35 and 35'. It is normally driven from 20-30 KZ, and in the embodiment, 25 KZ.

The term "excitation" is used to describe the field as well as "drive field", "modulation field" because any magnetic material within this field will oscillate at the frequency of the Helmholtz drive frequency therefore it is modulated or driven.

To measure any response within the surrounding field, a pair of receive coils 36 and 36', either planner or circular, are mounted conveniently to be physically as close as possible to the affected materials to be quantified. In the embodiment, for a paramagnetic labeled biomolecule, one moves region of interest 210 or a multitude of regions into the cylinder 310 containing the pair of permanent magnets 32 and 32', pair of excitation coils 35 and 35', and pair of receiving coils 36 and 36', and measures the paramagnetic response and its harmonics with in the cylinder 310. The field free region 37 is where the paramagnetic particles are not magnetically saturated, i.e., not magnetized, but oscillate and overcome Brownian and Neel relaxation, giving off not only the fundamental excitation frequency 25 KZ but harmonics of that frequency that are signature of the particle size and material. The signal is a linear quantification of the number of particles and their spatial location.

In the second embodiment of the superparamagnetic particle imaging analyzer of the present invention as shown in FIGS. 11A and 11B, the analyzer is an open-sided analyzer.

Similar to magnetic resonance imaging, superparamagnetic particle imaging requires homogeneous magnetic fields. For imaging in magnetic resonance imaging, the field of views (FOV) information from a detector or an array of detectors is stitched together (known as tomography) and presented as a 3-dimensional image created from contrast agents or from tissue itself. Magnetic resonance imaging requires large magnetic fields and radio frequency (RF) coils to accommodate access to the centroid of these fields. In comparison, superparamagnetic labels behave much differently in the superparamagnetic particle imaging analyzer of the present invention: it does not measure the proton alignment perturbed by an RF field, instead, it quantifies the non-linear magnetization of paramagnetic particles in a Field Free Region, where only Brownian and Neel relaxation dominate the field orientation of each particle. The AC field of the excitation coils of a particular frequency, for example ~25 Kz, switch the particle's magnetic poles rabidly from + to − at that fundamental rate M(t). The fundamental frequency of excitation generates not only an induced field, but harmonics that are a function of the particle material characteristics and size. The harmonic spectrum is a fingerprint and location of each magnetic label. (See Gleich, B., 2005; Goodwill, P., et al., "Multidimensional X-Space Magnetic Particle Imaging," IEEE Trans Med Imaging, 30(9): 1581-1590 (2011); and Knopp, T., et al., 2012)

In the second embodiment of the superparamagnetic particle imaging analyzer of the present invention as shown in FIGS. 11A and 11B, typical geometry of three-dimensional imagining device for small animals and humans as disclosed (Gleich, B., 2005; Goodwill, P., 2011; Konkle J., "Magnetic Particle Imaging with Advanced Tomographic Reconstruction Methods," Ph.D Thesis, University of California, Berkeley (2014)) is improved and merged with a new methodology, the hybrid point of care chip of the present invention. Instead of a Field Free Point or Region (FFP or FFR) 37 of the embodiment shown in FIGS. 10A and 10B, a linear area of a neutral field free region is created, referred to as FFL 37'. Improved access is provided to FFL 37' from the second embodiment compared to a cylindrical mid-point expands designs for mechanical placement, quantification and imaging. FFL 37' is accessible to other than a region of interest placed in a co-linear cylinder, which limits mechanical movement in all axes.

As shown in FIG. 11A, housing 31 is the mechanical support for the superparamagnetic particle imaging analyzer 30 of the present invention and consists of a C-shaped frame 311 constraining a linear field free region-forming pair of permanent NdFeB magnetics 32 and 32', forming the linear field free region by mechanically forcing the positive or negative poles of each magnet facing each other.

Figure 14:
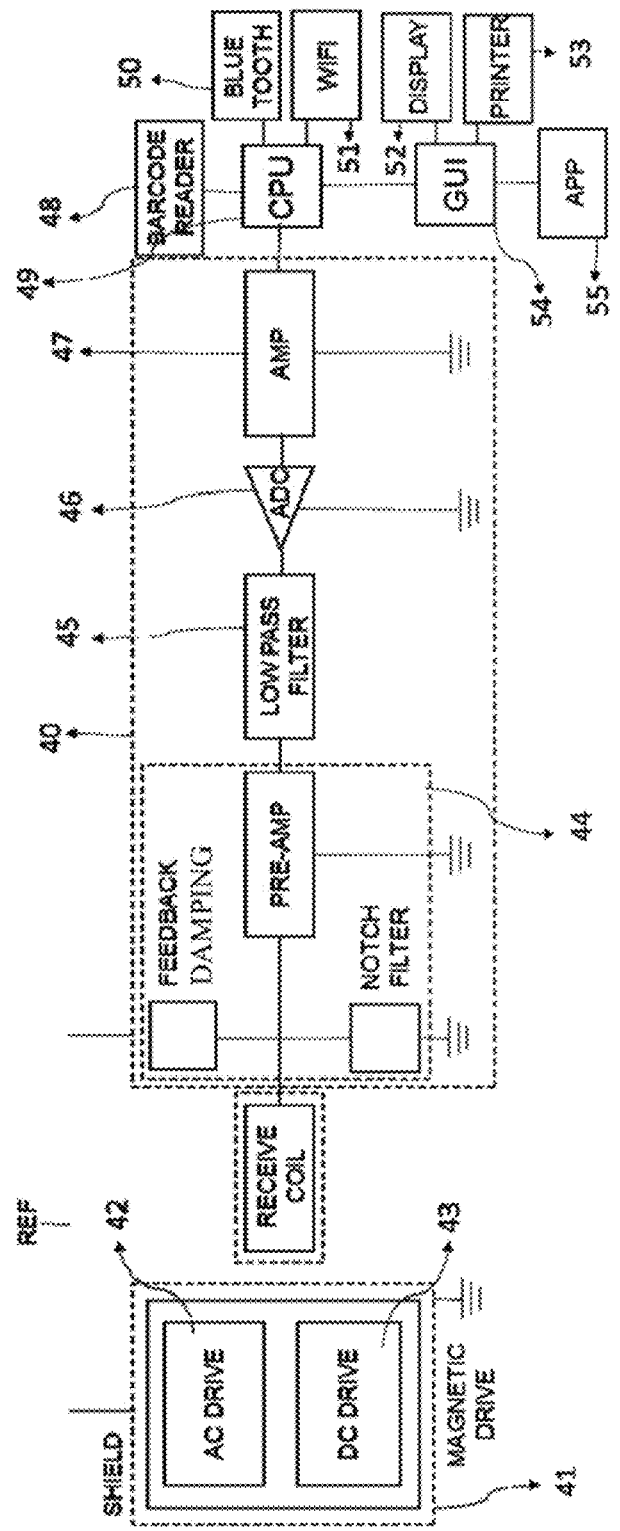
FIG. 14 is a diagram illustrating the signal chain in the superparamagnetic particle imaging analyzer of the present invention.

In the second embodiment, the magnets are rectilinear in shape, giving the rectilinear shape to the FFL 37'. A Helmholtz pair of coils 35 and 35' and a parallel pair of receive coils 36 and 36', again in a Helmholtz configuration, sense the induced magnetic field from the paramagnetic labels of analytical region 210 within the fundamental excitation region and the resulting harmonics. Analytical regions 210 of the hybrid point of care chip 20 of the present invention are transported in close contact to the induction coils (also referred to as excitation coils) 35 and 35', producing a measurable signal as shown in FIG. 14. The hybrid point of care chip 20 has sample and reagent handling capabilities (sample introduction region 21) that is distributed by switching column 24 to the capture analytical columns 210 and to fluid absorption area (shown in FIG. 9A).

The analyzer of the second embodiment and analytic method go beyond the point of care design limitations of Lateral Flow and Microfluidic devices. The linearity of most conventional assays are not required and thus limiting in the analyzer of the present invention, which is accomplished by the embodiment as shown in FIGS. 11A and 11B, where access to a rapidly moving FFL or to a mechanical scanning of the region of interest in a FFL space allow one to produce a metric of the number of paramagnetic labels, their status (bound or unbound) and to their location within the region of interest.

In the third embodiment of the superparamagnetic particle imaging analyzer of the present invention as shown in FIGS. 12A and 12B, analyzer 30 has an "E" core excitation field for the superparamagnetic particle imaging analyzer. To simplify the excitation coils 35 and 35' in the second embodiment as shown in FIGS. 11A and 11B and to produce an extremely homogenous AC transmit or modulation field, analyzer 30 use a pair of sintered Iron ferrite cores 35a and 35a' in the shape of an E, facing each other and separated by a ceramic insulator (not shown). Solenoid coil windings 35b and 35b' on each leg of the E core produce a field on the 2 diametrically opposed poles of the E-shape cores 35a and 35a' that are shortened to form a gap. Solenoid windings 35b and 35b' are run at an AC frequency with a feedback loop to the drive electronics (also refer to FIG. 14). This is the modulation field to excite and oscillate the magnetic labels of the hybrid point of care chip as described in FIG. 6A. A pair of superimposed permanent magnets 32 and 32' are forced to face each other with mutual positive poles to produce an FFR or FFP 37 within the gap of the E-core. All materials within the DC field are magnetized except in the neutral region of the FFR 37. The hybrid point of care chip 20 is moved through the gap and the accessible region. The AC induction of the paramagnetic labels produces the fundamental frequency of the AC field and the resulting harmonics, these are measured by the receiving coils 36 and 36' and passed on to the signal chain electronics. The third embodiment using the E core design in combination with the hybrid point of care chip of the present invention is an improved design because of the access to the AC excitation and the receiving coils giving superior SNR (signal to noise).

In the fourth embodiment of the superparamagnetic particle imaging analyzer of the present invention as shown in FIGS. 13A and 13B, the analyzer is a single sided superparamagnetic particle imaging analyzer with two concentrically placed transmit coils and separate receive coils. Unlike other embodiment, permanent magnets are not used in this embodiment. In the embodiment, analyzer 30 has a single sided pair of Helmholtz coils, resulting usefulness of the hybrid point of care chip 20 and its interaction with the formed 1D field of view (FOV) 38. A circular outer DC drive field is surrounded by a Helmholtz pair of an AC field. Arrows 39 in FIG. 13A indicates the selection field generated by DC currents in opposite directions. It creates opposite fields and forms a symmetrical FFR 37. When the hybrid point of care chip 20 passes over the field of view of the receiving coil 36, SPNP in the analytical region in FFR 37 will be excited and generate the signals. The advantage of using a Helmholtz coil is that it acts as an excitation coil and receive coil at the same time. Analytical region 210 passes over the sensor in a gradiometer fashion or is brought to a single position and measured.

FIG. 14 illustrates the signal chain and the communication to the end user of an AC coil-based superparamagnetic particle imaging analyzer and hybrid point of care technology of the present invention such as the embodiments shown in FIGS. 10, 11, and 12. As shown in FIG. 14, shield 41 is used to provide magnetic shielded field drives, including AC drive field 42 and DC drive field 43. Both AC drive field 42 and DC drive field 43. Magnetic resonance signal is sensed and sent in receive coil 36, and the fundamental frequency or frequencies of the signal is processed, and harmonics are separated from the emitted signal in signal preamplification unit 44 where the harmonics having very small voltage is converted by using a preamplifier, including notch filters and lock-in-amplifiers. Many of these devices can now be purchased as individual chip packages reducing individual circuit boards. Conventionally, the 1/f thermal noise is reduced at signal noise reduction and crosstalk step through low pass filter 45, and the pre-amplified voltage is converted by Analog to Digital conversion circuit 46, linearly amplified by signal amplifier 47, and sent to an external central processing unit (CPU) 49.

Two-dimensional barcodes as read by barcode reader 48 identifies the type of hybrid point of care, manufacturing date, user, and importantly, the working curve based from each manufacturing lot and makes decisions about the quality and sensitivity of the hybrid point of care assay. These quantitative results are available as blue tooth 50 or wireless signal output 51 information, as wired signal to a graphical user interface (GUI) 54 (to be used by operator and hospital information system (HIS)). Graphical user interface 54 handles input, for example an on-board GPS, time of assay performance, record and data management to portable memory devices or databases.

Graphical user interface 54 controls traditional displays 52 on touch screen panels, wirelessly prints out hard copies of results and databases by printer 53, and additionally communicates with a fully developed mobile Application 55 that provides results, location, suggested interpretation and history of data. The feature allows graphical manipulation of multiple data points in a real time, mobile environment in the mobile Application 55.

The fifth embodiment of the superparamagnetic particle imaging analyzer of the present invention is shown in FIGS. 15A to 15D, where the analyzer is a permanent NdFeB magnet with a Hall sensor. In analyzer 30, a NdFeB cylindrical permanent magnetic 32 is mounted (with phantom magnetic field lines 63 for illustrative purposes). The lines of force 63 are in a homogeneous field of quanta energy surrounded and formed by any magnetic source, they are not observable, much like gravitational force fields and are only in FIGS. 15A and 15B to describe the fields and their distribution.

The NdFeB magnet 32 has magnetic lines 63 that leave the South pole of the magnet and fold around to the North pole of the permanent magnet. These poles are only named by conventional purpose. A Hall probe sensor 60 is placed in a null free region 37b where the lines of force 63 leaving the circular magnet 32 reach a theoretical null region at the precise center of the cylinder 33a and of the force fields. Mounting of Hall probe within cylinder 33a and onto a non-magnetizable hollow shaft 71 allows the bias leads and signals 62 to be routed to the signal processing electronics much like in FIG. 14 but without drive fields, the permanent magnetic provides the DC field as oppose the coils sets, which greatly simplify the design and manufacturing of the device. There are no harmonics generated because the field is similar to a driven DC field forming a Field Free Region 37. In the null region 37b, there is little or no theoretical magnetic area, only narrow fringe fields.

In the present invention, the superparamagnetic particle imaging analyzer works with the hybrid point of care chip, by transporting the chip 20 and the analytical regions 210 over the sensor 60, either in a gradiometer fashion or as a single measurement, the magnetic labels of the analytical regions are magnetized by collapsing the null field 37b and producing an induced signal to Hall magnetic sensor 60. The signal can be quantified or processed to produce an image.

Figure 15B:
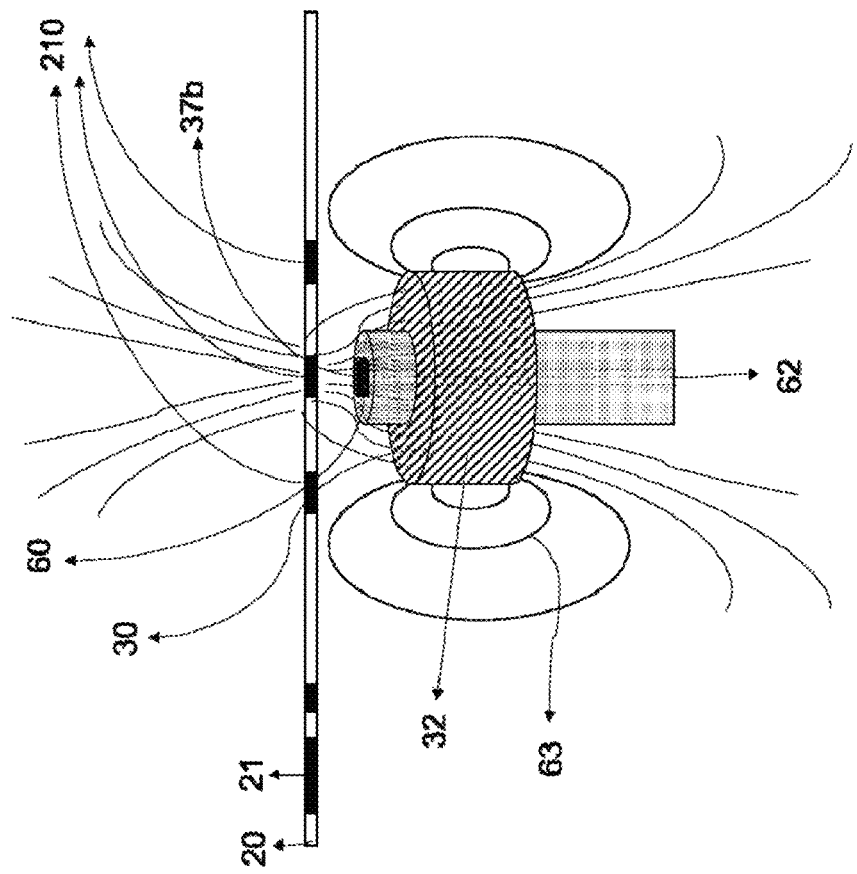
FIG. 15B is a partial top view showing the permanent magnet and the hybrid point of care chip of the present invention as a disposable member of the analyzer and used in relation to the permanent magnet.
Figure 15A:
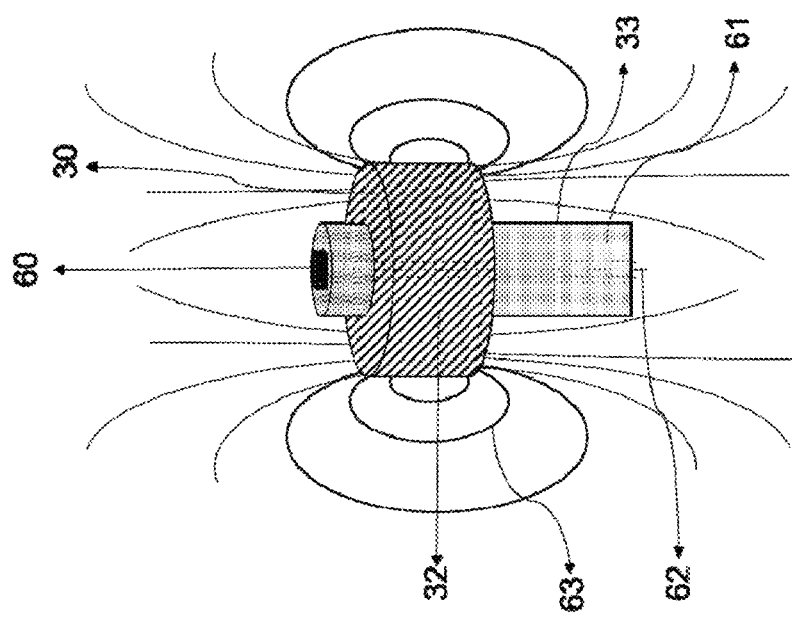
FIG. 15A is a partial side view showing structure of the permanent magnet used in a fifth embodiment of the superparamagnetic particle imaging analyzer of the present invention where the analyzer is a Hall sensor analyzer.

FIGS. 15C and 15D show construction images of a superparamagnetic particle imaging analyzer with a hybrid point of care chip in the present invention. Permanent magnet 32 is a NdFeB magnet that is supported by hollow shaft 61 which is a hollow nonmagnetic Hall sensor shaft; and fields of force elucidated by lines 63 in FIGS. 15A and 15B are formed in cylinder 33a of magnet 32. Exterior support and shield 41 of the instrument of the superparamagnetic particle imaging analyzer 30 houses hollow shaft 61. Hollow shaft 61 routes the voltages for Hall magnetic sensor 60 and the output signal, and at the same time is the mount of the probe within the null field 37b of permanent magnet 32.

The hybrid point of care chip 20 of the present invention as describe in details in FIGS. 9A to 9D is shown in FIGS. 15C and 15D in the side and top views as being transported across the Hall magnetic sensor 60 and generating a gradiometer or spatially encoded signal, which is then processed by CPU 49 and displayed by GUI 54 as shown in FIG. 14. Top view of FIG. 15D illuminates the relationship of the analytic regions 210a, 210b, and 210c, passing over or statically measured over Hall magnetic sensor 60.

Figure 16:
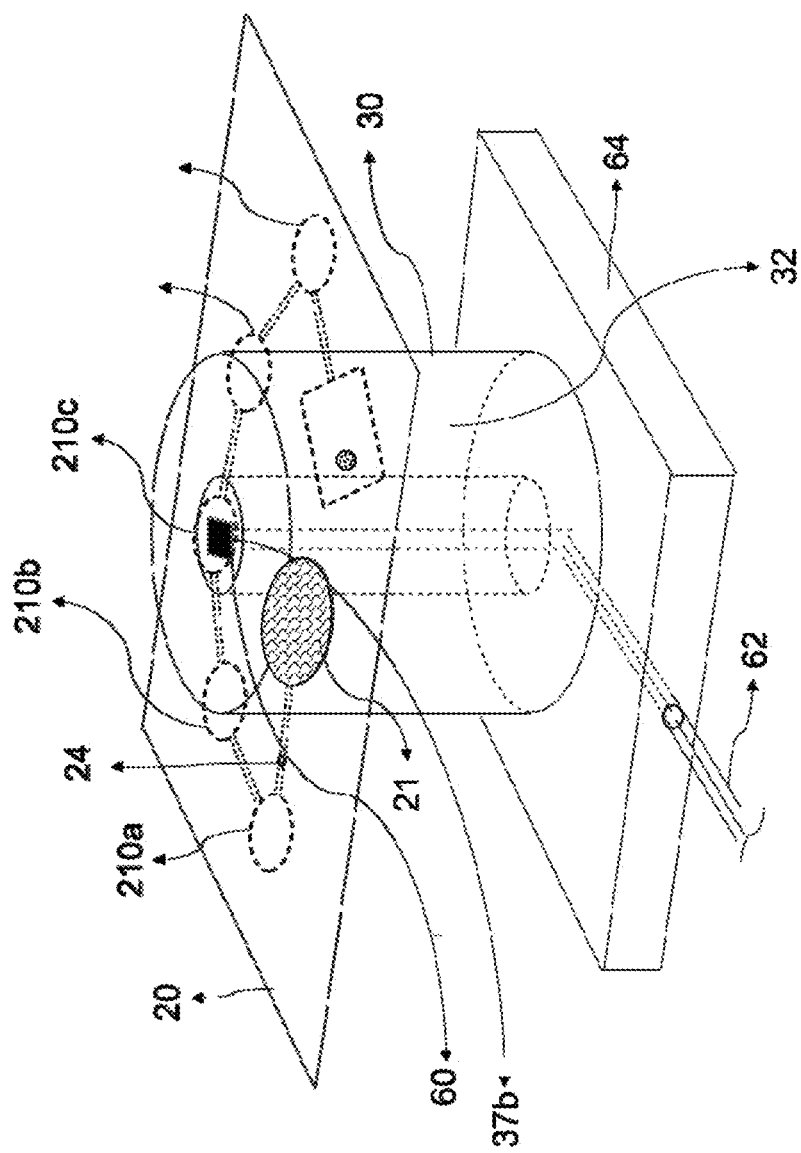
FIG. 16 shows structure of the sixth embodiment of the superparamagnetic particle imaging analyzer used with the nonlinear hybrid point of care chip of the present invention.

The sixth embodiment of the superparamagnetic particle imaging analyzer 30 working with the nonlinear hybrid point of care chip 20 of the present invention is illustrated in FIG. 16. In the sixth embodiment, analyzer 30 is supported on a supporting base 64. Analytical regions 210a to 210e of chip 20 are moved into null region 37b sequentially in a manner of circular arc in relationship to an accessible superparamagnetic particle imaging permanent magnet 32 and Hall magnetic sensor 60 as described in FIGS. 15A and 15B. Generated signals go through Hall probe bias leads and output signal 62. The format of permanent magnet 32 and nonlinear analytical chip 20 reduces the overall cost, while the analytical regions 210 can be multiplexed and imaged with a priori knowledge of spatial construction. Reconstruction techniques used in Computed Tomography demonstrates possible 3D imaging with Hall magnetic sensor 60 or a multitude of sensors in the Null region 37b, each with a FOV (Field of View) contributing to the mathematical models. Supporting base 64 of analyzer 30 is a first order non-magnetic material which induces and distributes the field lines of the NdFeB magnet 32, while Hall probe bias leads and output signal 62 go through supporting base 64.

Figure 17:
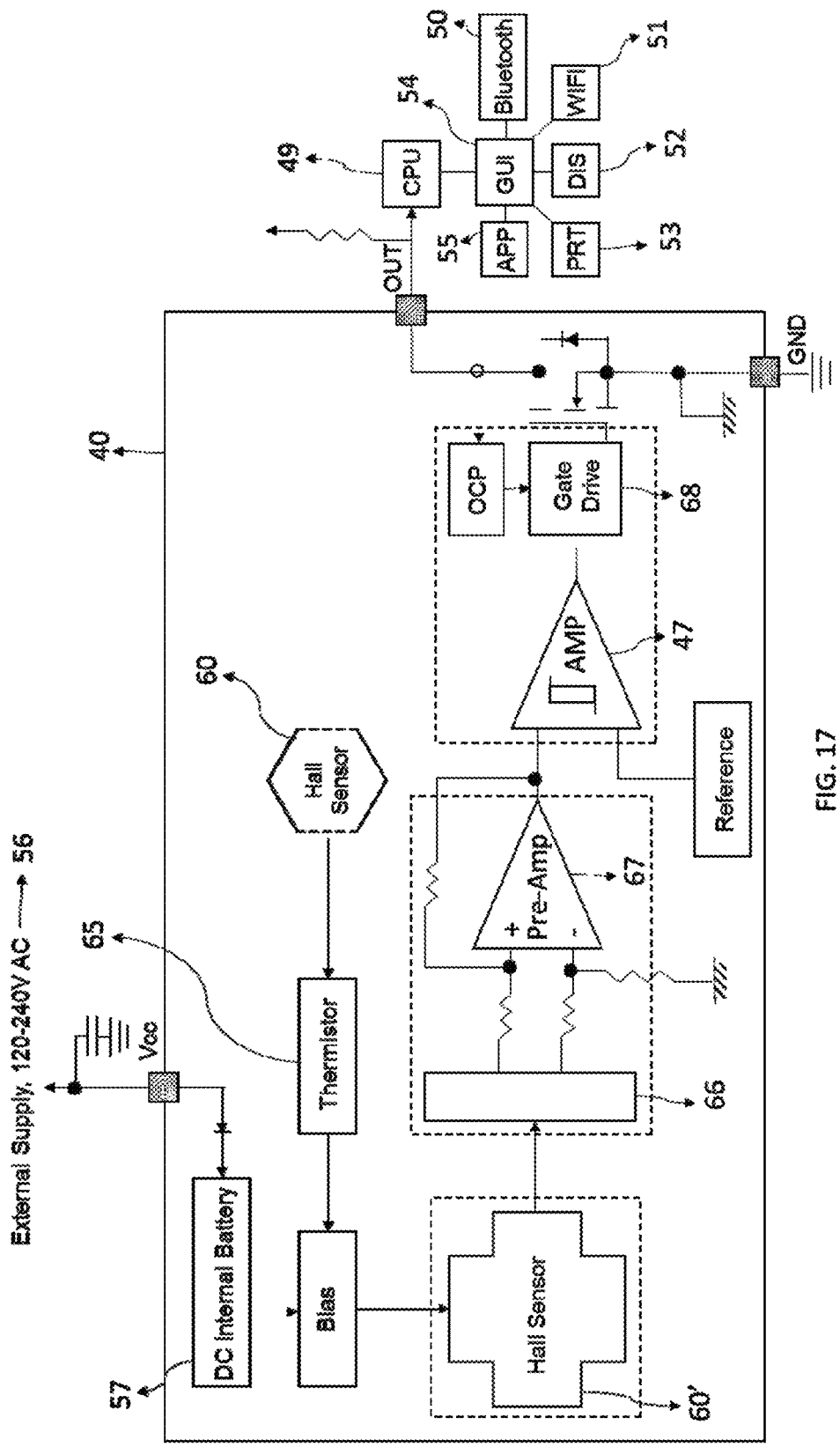
FIG. 17 is a diagram illustrating the signal chain in the superparamagnetic particle imaging analyzer of the present invention based on Hall sensor.

As shown in FIG. 17, signal chain 40 is outlined showing one example to measure a sensor signal from a magnetic field. In signal chain 40, plug-in transformer 56 from a 120-240 AC wall source or internal battery 57 provides the DC bias voltage to a Hall sensor 60'. Thermistor 65 corrects for temperature of the environment of the instrument, additional Hall sensor 60 corrects for any magnetic field, including the Earth's, in the vicinity of the instrument. Once the Hall sensor produces a signal or voltage, it is filtered by Offset Cancel Integrated circuit feedback loop of filter 66 and passed on to a preamplifier 67 that is closely coupled to a linear amplifier 47. The amplified signal is low power matched with a gate drive 68 and over current protection (OCP) to input of a central processing unit (CPU) 49 that controls the graphical user interface (GUI) 54 or user input. GUI 54 is the human interface that directs the measured magnetic signal from the Hall Element 60' to be sent to Application or program 55, Printer 53, Display 52, Blue Tooth device 50, or a wireless communication 51, for example the internet or cloud.

Example 1. Dose Response of Rabbit IgG Conjugated SPNP on the HY-POC Chip of the Present Invention Materials:

In this example, materials used include Rabbit IgG 150K (Arista Bio, AGRIG-0100, lot 091325551, 2.88 mg/ml); Goat Anti-Rabbit IgG (H&L) Antibody, Purified (BioSpacific: G-301-C-ABS, lot WEB08, 6.39 mg/ml); Magnetic beads (MicroMod, 09-02-132, 130 nm, 10 mg/ml); Silica beads (CORPUSCULAR C—SiO-10COOH, 10 micron sphere, 10 mg/ml); Nitrocellulose membrane (Millipore HF180UBXSS, lot R6EA62198C); N-Hydroxysulfosuccinimide sodium salt (Sulfo-NHS) (Combi-Blocks Cat: OR-6941; Cas. #106627-54-7); 1-(3-Dimethylaminopropyl)-3-ethylcarbodiimide hydrochloride (EDC) (AK Scientific Cat #965299); bovine serum albumin (BSA); Tween-20; Coupling Buffer: 10 mM PBS pH 7.4; Storage Buffer (10 mM PBS, 0.6 mg/ml BSA, 0.05% NaN3); Sample running buffer (10 mM PBS, 1 mg/ml BSA, 0.1% tween-20).

Methodology:

1. Preparation of magnetic beads labeled Rabbit IgG (R-IgG-SPNP): 0.1 ml 10 mg/ml 130 nm magnetic beads are added in the 1.5 ml tube, followed by 0.2 ml PBS coupling buffer, and then 0.01 ml EDC (10 mg/ml) and 0.01 ml NHS-Sulfo (10 mg/ml) to the above solution. The mixture is allowed to react at room temperature for 20 minutes with continuous mixing. Then, 0.57 ml Rabbit IgG (2.88 mg/ml) is added to the mixture and the mixture is rotated at room temperature for 2 hrs. Then, the beads are pulled down with magnetic separator, washed with 2×0.5 ml PBS, and suspended in 1 ml storage buffer to get R-IgG-SPNP.

2. Preparation of Stationary Phase: Anti-Rabbit IgG (GAR) antibody covalently conjugated silica beads: 0.1 ml 10 mg/ml 10 micron carboxylic acid silica beads is added in the 1.5 ml tube, followed by 0.2 ml PBS coupling buffer, and 0.01 ml EDC (10 mg/ml) and 0.01 ml NHS-Sulfo (10 mg/ml) to the above solution to form a mixture. The mixture is allowed to react at room temperature for 20 minutes with continuous mixing. Then, 0.156 ml Goat Anti-Rabbit-IgG (6.39 mg/ml) is added to the mixture. The mixture is rotated at room temperature for 2 hrs, followed by centrifuge at 13,000 RPM for 3 minutes and removal of supernatant. Then, the silica beads are washed with 2×0.5 ml PBS and dried at 35° C. for 12 hours.

3. Preparation of Anti-Rabbit IgG (GAR) antibody adsorbed silica beads: 0.1 ml 10 mg/ml 10 micron carboxylic acid silica beads are added in the 1.5 ml tube, followed by 0.2 ml PBS coupling buffer and 0.005 ml Goat Anti-Rabbit-IgG (6.39 mg/ml). The mixture is rotated at room temperature for 12 hrs and centrifuged at 13,000 RPM for 3 minutes. Then, supernatant is removed, and the silica beads are washed with 2×0.5 ml PBS and dried at 35° C. for 12 hours.

4. Preparation of Anti-Rabbit IgG (GAR) antibody adsorbed nitrocellulose disks: 0.2 ml PBS is added in the 1.5 ml tube, followed by 0.003 ml Goat Anti-Rabbit-IgG (6.39 mg/ml) and pre-formed nitrocellulose disks. The mixture is rotated at room temperature for 2 hrs, and the solution is removed. The nitrocellulose disks are dried at 35° C. for 12 hours.

Figure 18:
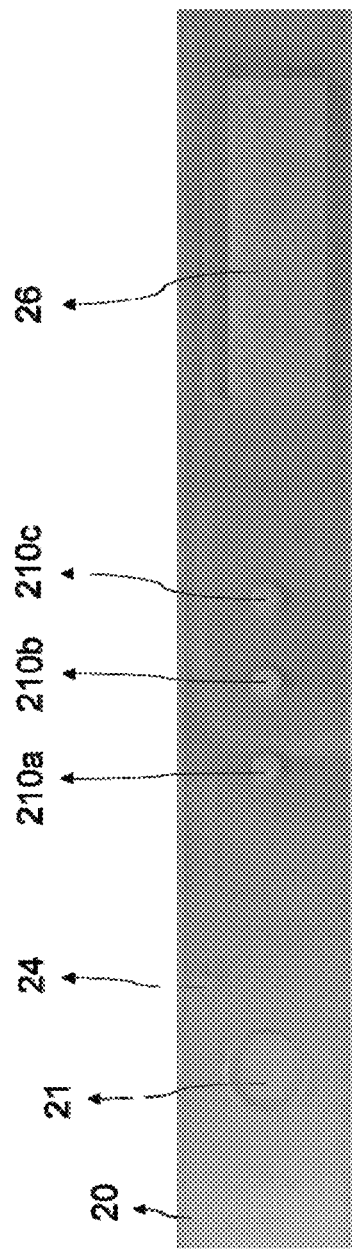
FIG. 18 shows the hybrid point of care chip of the present invention used in Example 1.

5. Construction of Rabbit IgG hybrid point of care chip: as shown in FIG. 18, a hybrid point of care chip 20 of the present invention is assembled. In chip 20, switching column 24 is filled with plain 10 micron carboxylic acid silica beads. The first analytical region 210a is filled with GAR antibody covalently conjugated silica beads as stationary phase. The second analytical region 210b is filled with GAR antibody adsorbed silica beads as stationary phase. The third analytical region 210c is filled with GAR antibody adsorbed nitrocellulose disks as stationary phase.

The construction of this chip demonstrated two different methods of making stationary phase: dispensing particles as in the first and second analytical regions 210a and 210b, or placing the pre-formed material as in the third analytical region 210c. It also demonstrated two different methods of loading the immobilizing matrix on stationary phase: covalent bonding as for the first analytical region 210a, or physical adsorption as for the second and third analytical regions 210b and 210c.

6. Preparation of sample running solution: the sample running buffer is used to dilute 130 nm magnetic beads labeled Rabbit IgG (1 mg/ml) to appropriate concentration. The concentrations of the samples are: 0, 10, 20, 30, 40, 50, 60, 70, 80, 90, 100 ng/ml.

7. Running an assay: pipette 0.01 ml of sample running solution and add the solution to the sample introduction region. Wait until the sample introduction region is empty (3-5 minutes). Then, 0.01 ml sample running buffer is added. Then, wait until the sample introduction region is empty (3-5 minutes), and then, read the chip with an SPI instrument. 8. Reading the hybrid point of care chip: hybrid point of care chips are analyzed by an SPI analyzer. All three analytical regions 210a, 210b, and 210c are analyzed in a single scan in 17 seconds.

Experimental Results and Discussion

Experimental results are displayed in FIG. 19, demonstrating that SPNP labeled Rabbit IgG samples (R-IgG-SPNP) with different concentrations are analyzed on the hybrid point of care chip of the present invention. The results in FIG. 19 show that the Rabbit IgG is captured on all three analytical regions, and magnetic signals are proportional to the SPNP concentrations. The sample flows through the hybrid point of care chip 20 automatically without any pump. The assay time is less than 10 minutes. The sample size can be less than 10 microliter. Different material (silica beads and nitrocellulose membrane) can be used as stationary phases to immobilize the analyte (Rabbit IgG). Different methods of functionalizing the stationary phase (covalent bond and physical adsorption) can be used to load capturing material. And different stationary phase packing methods (in situ filling and pre-form) can be used in manufacturing the hybrid point of care chips.

We claim:
1. A superparamagnetic nanoparticle-based analytical method, comprising
providing a sample comprising at least one or more analytes,
providing a point of care chip comprising at least one or more analytical regions, wherein each analytical region is a stationary phase having at least one or more sections of immobilizing matrix,
labeling each of the analytes in the sample with a superparamagnetic nanoparticle and immobilizing the labeled analytes to the immobilizing matrix in the analytical regions on the point of care chip,
providing an analytical device, wherein the analytical device comprises a first means for generating a field free zone, a second means for exciting the superparamagnetic nanoparticles in vitro, and a third means for sensing, receiving, and transmitting response of the excited superparamagnetic nanoparticles,
providing a changing external magnetic field in the analytical device by the second means for exciting the superparamagnetic nanoparticles, wherein the changing external magnetic field has one single frequency,
providing the field free zone in the changing external magnetic field by the first means for generating the field free zone and passing the immobilizing matrix with the labeled analytes on the point of care chip through the field free zone, and at same time, exciting the superparamagnetic nanoparticles on the labeled analytes in the field free zone by the second means for exciting the superparamagnetic nanoparticles to generate a spatially encoded response, wherein the spatially encoded response correspond to the immobilized location of the labeled analytes in the analytical regions,
sensing, receiving, and transmitting the spatially encoded response of the superparamagnetic nanoparticles by the third means for sensing, receiving, and transmitting response of the excited superparamagnetic nanoparticles, and
analyzing the spatially encoded response of the superparamagnetic nanoparticles to determine characteristics of the analytes, wherein the spatially encoded response comprises harmonics and are determined by shape, coating, size, and immobilized or free state of the superparamagnetic nanoparticles.
2. The superparamagnetic nanoparticle-based analytical method according to claim 1, further comprising quantitatively determining the characteristics of the analytes based on the spatially encoded response of the superparamagnetic nanoparticles.

3. The superparamagnetic nanoparticle-based analytical method according to claim 1, wherein the stationary phase consists of one single immobilizing matrix.

4. The superparamagnetic nanoparticle-based analytical method according to claim 1, wherein the stationary phases are adopted to immobilize different types of analytes in a range of 1 to 20.

5. The superparamagnetic nanoparticle-based analytical method according to claim 1, wherein each of the superparamagnetic nanoparticles corresponds to each of the labeled analytes and is distinct from other superparamagnetic nanoparticles on the labeled analytes in the sample.

6. The superparamagnetic nanoparticle-based analytical method according to claim 1, wherein the superparamagnetic nanoparticle has a particle size in a range of 1 nm to 1000 nm.

7. The superparamagnetic nanoparticle-based analytical method according to claim 1, wherein the superparamagnetic nanoparticle is made of Fe, CoFe, Co, Co alloy, ferrite, cobalt nitride, cobalt oxide, Co—Pd, Co—Pt, iron, iron alloy, Fe—Au, Fe—Cr, Fe—N, FeO, Fe—Pd, Fe—Pt, Fe—Zr—Nb—B, Mn—N, Nd—Fe—B, Nd—Fe—B—Nb—Cu, Ni, or Ni alloys.

8. The superparamagnetic nanoparticle-based analytical method according to claim 1, wherein the analytical region is of an assay format that is hybrid point of care, lateral flow, microfluidic bead, or ELISA monolayer.

9. The superparamagnetic particle imaging analyzer to be used in the analytical method of claim 1, comprising
   two concentrically placed transmit coils, and
   receive coil,
   wherein the analyzer is a single sided analyzer,
   currents in the two transmit coils are in opposite directions and form field lines with a field free region symmetrical to the field lines, the sample having the superparamagnetic nanoparticle labeled analytes are placed in the field free region for excitation, and the paramagnetic response of the superparamagnetic nanoparticle are sensed and transmitted by the receive coil.

10. The superparamagnetic particle imaging analyzer to be used in the analytical method of claim 1, comprising
    a non-magnetizable hollow shaft,
    a permanent magnet in a shape of a cylinder, having a cylindrical interior inside, and being mounted and supported by the non-magnetizable hollow shaft therethrough, and
    a Hall sensor having bias leads and signals and being placed in the cylindrical interior of the permanent magnet and onto the non-magnetizable hollow shaft,
    wherein the permanent magnet has theoretical lines of magnetic force to create a magnetic force field, wherein the lines of magnetic force leaving the cylindrical permanent magnet create a null region at center of the cylinder and of the magnetic force fields,
    the permanent magnet provides induction to the sample having the superparamagnetic nanoparticle labeled analyte in the null region, and
    the Hall sensor is placed in the null region at the center of the cylindrical interior, senses and receive the paramagnetic response of the superparamagnetic nanoparticles, and the bias leads and signals of the paramagnetic response are sent out for signal processing.

* * * * *